United States Patent [19]
Alitalo et al.

[11] Patent Number: 5,955,291
[45] Date of Patent: Sep. 21, 1999

[54] ANTIBODIES RECOGNIZING TIE RECEPTOR TYROSINE KINASE AND USES THEREOF

[76] Inventors: Kari Alitalo, Nyyrikintie 4 A, FIN-00210 Espoo; Juha Partanen, Hiihtomäentie 46 A 15, SF-00800 Helsinki; Tomi Mäkelä, Haahkatie 3 A 8, SF- 00200 Helsinki; Jaana Korhonen, Agricolankatu 7 C 68, SF-00530 Helsinki; Marja-Terttu Matikainen, Lankkistentanhua 12, FIN-23100 Mynamaki, all of Finland

[21] Appl. No.: 08/220,240

[22] Filed: Mar. 29, 1994

Related U.S. Application Data

[63] Continuation-in-part of application No. PCT/FI93/00006, Jan. 8, 1993, and application No. 08/167,453, Dec. 15, 1993, abandoned, which is a continuation of application No. 07/817,800, Jan. 9, 1992, abandoned.

[51] Int. Cl.$^6$ ............... G01N 33/574; A61K 39/395; C12P 21/08; C07K 16/00
[52] U.S. Cl. ............... 435/7.23; 424/133.1; 424/155.1; 530/387.3; 530/387.7
[58] Field of Search ............... 435/7.23, 240.2; 424/133.1, 1.49, 155.1; 530/387.1, 387.3, 388.1, 388.22, 389.1, 391.3, 391.7

[56] References Cited

FOREIGN PATENT DOCUMENTS

WO9314124  7/1993  WIPO.
WO 95/26364  10/1995  WIPO ............... C07K 16/40

OTHER PUBLICATIONS

Kimball. Introduction to Immunology, 3rd ed., p. 141, 1990.
Queen et al. "A humanized antibody that binds to the interleukin 2 receptor" PNAS vol. 86. p. 10029–10033.
Andersson et al., "Structural and Functional Markers During Induced Differentiation in Human Leukemia Cell Lines," in *Expression of Differentiated Functions in Cancer Cells*, pp. 239–245. (Revoltella, ed., Raven Press, New York) (1982).
Appella et al., "The Receptor–Binding Sequence of Urokinase," *J. Biol. Chem.*, 262(10):4437–4440 (Apr. 5, 1987).
Armstrong et al., "Expression of Tie Receptor Tyrosine Kinase in Leukemia Cell Lines," *Leukemia*, 7(10):1585–1591 (Oct., 1993).
Bazan, "Structural Design and Molecular Evolution of a Cytokine Receptor Superfamily," *Proc. Natl. Acad. Sci. (USA)*, 87:6934–6938 (Sep., 1990).
Berridge et al., "Cell–Lineage Antigens of the Stem Cell–Megakaryocyte–Platelet Lineage are Associated with the Platelet IIb–IIIa Glycoprotein Complex," *Blood*, 66(1):76–85 (Jul., 1985).
Bradley et al., "Cell Lines Derived from a Human Myelomonocytic Leukaemia," *Br. J. Haemat.*, 51:595–604 (1982).
Cole et al., "The EBV–Hybridoma Technique and its Application to Human Lung Cancer," in *Monoclonal Antibodies and Cancer Therapy*, pp. 77–96 (Alan R. Liss, Inc.) (1985).
Collins et al., Continuous Growth and Differentiation of Human Myeloid Leukaemic Cells in Suspension Culture., *Nature*, 270:347–349 (Nov. 24, 1977).
Cunningham et al., "Neural Cell Adhesion Molecule: Structure, Immunoglobulin–Like Domains, Cell Surface Modulation, and Alternative RNA Splicing," *Science*, 236:799–806 (May 15, 1987).
Davis, "The Many Faces of Epidermal Growth Factor Repeats," *The New Biologist*, 2(5):410–419 (May, 1990).
Devereux et al., "A Comprehensive Set of Sequence Analysis Programs for the VAX," *Nucleic Acids. Res.*, 12(1):387–395 (1984).
Edgell et al., "Permanent Cell Line Expressing Human Factor VIII–Related Antigen Established by Hybridization," *Proc. Natl. Acad. Sci.* (USA) 80:3734–3737 (Jun., 1983).
Emeis and Edgell, "Fibrinolytic Properties of a Human Endothelial Hybrid Cell Line. (Ea.hy 926)," *Blood*, 71(6):1669–1675 (Jun., 1988).
Feinberg and Vogelstein, "A Technique for Radiolabeling DNA Restriction Endonuclease Fragments to High Specific Activity," *Anal. Biochem.*, 132:6–13 (1983).
Frackelton et al., "Generation of Monoclonal Antibodies Against Phosphotyrosine and Their Use for Affinity Purification of Phosphotyrosine–Containing Proteins," *Methods in Enzymology*, 201:79–92 (1991).
Furie and Furie, "The Molecular Basis of Blood Coagulation," *Cell*, 53:505–518 (May 20, 1988).
Gahmberg et al., "Membrane Glycosylation During Cell Differentiation," in *Gene Expression During Normal and Malignant Differentiation*, pp. 107–123 (Academic Press, Inc., London) (1985).
Greenberg et al., "Characterization of a New Megakaryocytic Cell Line: The Dami Cell," *Blood*, 72(6):1968–1977 (Dec., 1988).
Greenfield et al., "Optimization of Immunotherapy with Adriamycin (Hydrazone)—Immunoconjugates in Human B–Lymphoma Xenografts," *Antibody, Immunoconjugates and Radiopharmaceuticals*, 4(2):107–119 (1991).
Haluska et al., "Localization of the Human JUN Protooncogene to Chromosome Region 1p31–32," *Proc. Natl. Acad. Sci. (USA)*, 85:2215–2218 (Apr., 1988).
Harper and Saunders, "Localization of Single Copy DNA Sequences on G–Banded Human Chromosomes by in situ Hybridization," *Chromosoma* (Berl.), 83:431–439 (1981).
Hirai et al., "A Novel Putative Tyrosine Kinase Receptor Encoded by the eph Gene," *Science*, 238:1717–1720 (Dec. 18, 1987).

(List continued on next page.)

*Primary Examiner*—Paula K. Hutzell
*Assistant Examiner*—Yvonne Eyler
*Attorney, Agent, or Firm*—Marshall, O'Toole, Gerstein, Murray & Borun

[57] ABSTRACT

The present invention relates to an anti-Tie monoclonal antibody, 3C4C7G6, which is useful as a diagnostic tool for detecting angiogenesis-associated with neoplasia, wound healing, and a variety of other angiogenesis associated diseases and for radiological imaging of blood vessels. In addition, the disclosed antibody is useful as a therapeutic agent.

33 Claims, 3 Drawing Sheets

OTHER PUBLICATIONS

Kaipainen et al., "Enhanced Expression of the Tie Receptor Tyrosine Kinase Messenger RNA in the Vascular Endothelium of Metastatic Melanomas," *Cancer Research*, 54:6571–6577 (Dec. 15, 1994).

Katz et al., "The SJL/J T Cell Response to Both Spontaneous and Transplantable Syngeneic Reticulum Cell Sarcoma is Mediated Predominantly by the Vβ17a+ T Cell Clonotype," *J. Exp. Med.*, 168:1553–1562 (Nov., 1988).

Kelley et al., "Mutations Altering the Structure of Epidermal Growth Factor–Like Coding Sequences at the Drosphila Notch Locus," *Cell*, 51:539–548 (Nov. 20, 1987).

Kieffer et al., "Uncoupling in the Expression of Platelet GP IIb/IIIa in Human Endothelial Cells and K562 Cells: Absence of Immunologic Crossreactivity Between Platelet GP IIb and the Vitronectin Receptor Alpha Chain," *Blood*, 72 (4):1209–1215 (Oct., 1988).

Koeffler and Golde, "Acute Myelogenous Leukemia: A Human Cell Line Responsive to Colony–Stimulating Activity," *Science*, 200:1153–1154 (Jun. 9, 1978).

Köhler and Milstein, "Continuous Cultures of Fused Cells Secreting Antibody of Predefined Specificity," *Nature*, 256:495–497 (Aug. 7, 1975).

Korhonen et al., "The Mouse tie Receptor Tyrosine Kinase Gene: Expression During Embryonic Angiogenesis," *Oncogene*, 9:395–403 (1994).

Kozak, "Compilation and Analysis of Sequences Upstream from the Translational Start in Eukaryotic mRNAs." *Nucleic Acids Res.*, 12(2):857–872 (1984).

Kozbor and Roder, "The Production of Monoclonal Antibodies from Human Lymphocytes," *Immunology Today*, 4(3):72–79 (1983).

Lhoták et al., "Characterization of Elk, a Brain–Specific Receptor Tyrosine Kinase," *Mol. Cell Biol.*, 11:2496–2502 (May, 1991).

Lindberg and Hunter, "cDNA Cloning and Characterization of eck, an Epithelial Cell Receptor Protein–Tyrosine Kinase in the eph/elk Family of Protein Kinases," *Mol. Cell. Biol.*, 10:6316–6324 (Dec., 1990).

Lindmo et al., "Determination of the Immunoreactive Fraction of Radiolabeled Monoclonal Antibodies by Linear Extrapolation to Binding at Infinite Antigen Excess," *J. of Immunological Methods*, 72:77–89 (1984).

Lindmo et al., "Quality Control of Monoclonal Antibodies After Radiolabelling, The Fraction of Immunoreactive Antibody Determined at Infinite Antigen Excess," *European J. of Nucl. Med.*, 9:A77 (Abstract A468) (1984).

Lozzio and Lozzio, "Human Chronic Myelogenous Leukemia Cell–Line with Positive Philadelphia Chromosome," *Blood*, 45(3):321–334 (Mar., 1975).

Martin and Papayannopoulou, "HEL Cells: A New Human Erythroleukemia Cell Line with Spontaneous and Induced Globin Expression," *Science*, 216:1233–1235 (Jun. 11, 1982).

McCutchan and Pagano, "Enhancement of the Infectivity of Simian Virus 40 Deoxyribonucleic Acid with Diethyl–aminoethyl–Dextran," *J. Natl. Cancer Inst.*, 41(2):351–357 (Aug., 1968).

Miles and Hales, "Labelled Antibodies and Immunological Assay Systems", *Nature* 219:186–189 (Jul. 13, 1968).

Minowada et al., "Brief Communication: Rosette–Forming Human Lymphoid Cell Lines. 1. Establishment and Evidence for Origin of Thymus–Derived Lymphocytes" *J. Natl. Cancer Inst.*, 49(3):891–895 (Sep., 1972).

O'Bryan et al., "axl, a Transforming Gene Isolated from Primary Human Myeloid Leukemia Cells, Encodes a Novel Receptor Tyrosine Kinase," *Mol. Cell. Biol.*, 11(10):5016–5031 (Oct., 1991).

Partanen et al., "FGFR–4, a Novel Acidic Fibroblast Growth Factor Receptor with a Distinct Expression Pattern," *EMBO J.* 10(6):1347–1354 (1991).

Partanen et al., "Putative Tyrosine Kinases Expressed in K–562 Human Leukemia Cells," *Proc. Natl. Acad. Sci. (USA)*, 87:8913–8917 (Nov., 1990).

Poncz et al., "Cloning and Characterization of Platelet Factor 4 cDNA Derived from a Human Erythroleukemic Cell Line," *Blood*, 69(1):219–223 (Jan., 1987).

Sanger et al., "DNA Sequencing with Chain–Terminating Inhibitors," *Proc. Natl. Acad. Sci. (USA)*, 74(12):5463–5467 (Dec., 1977).

Scheinberg and Houghton, "Current Status of Antitumor Therapy with Monoclonal Antibodies," *Oncology*, 1(3):31–37 (May, 1987).

Schwenk and Schneider, "Cell Cycle Dependency of a T–Cell Marker on Lymphoblasts," *Blut*, 31:299–306 (1975).

Siegelman et al., "The Mouse Lymph Node Homing Receptor is Identical with the Lymphocyte Cell Surface Marker Ly–22: Role of the EGF Domain in Endothelial Binding," *Cell*, 61:611–622 (May 18, 1990).

Stacey and Schnieke, "SVpoly: A Versatile Mammalian Expression Vector," *Nucleic Acids Res.*, 18(9):2829 (1990).

Stanley and Luzio, "Construction of a New Family of High Efficiency Bacterial Expression Vectors: Identification of cDNA Clones Coding for Human Liver Proteins," *EMBO J.*, 3(6):1429–1434 (1984).

Staunton et al., "The Arrangement of the Immunoglobulin–Like Domains of ICAM–1 and the Binding Sites for LFA–1 and Rhinovirus," *Cell*, 61:243–254 (Apr. 20, 1990).

Stearns et al., "Microthrombomodulin," *J. Biol. Chem.*, 264(6):3352–3356 (Feb. 25, 1989).

Streuli et al., "A Family of Receptor–Linked Protein Tyrosine Phosphatases in Humans and Drosphila," *Proc. Natl. Acad. Sci. (USA)*, 86:8698–8702 (Nov., 1989).

Sundström and Nilsson, "Establishment and Characterization of a Human Histiocytic Lymphoma Cell Line (U–937)," *Int. J. Cancer*, 17:565–577 (1976).

Tepass et al., "crumbs Encodes an EGF–Like Protein Expressed on Apical Membranes of Drosphila Epithelial Cells and Required for Organization of Epithelia," *Cell*, 61:787–799 (Jun. 1, 1990).

Treisman et al., "A Single Amino Acid Can Determine the DNA Binding Specificity of Homeodomain Proteins," *Cell*, 59:553–562 (Nov. 3, 1989).

Trent et al., "Report of the Committee on Structural Chromosome Changes in Neoplasia," *Cytogenet. Cell Genet.*, 51:533–562 (1989).

Vässin et al., "The Neurogenic Gene Delta of *Drosphila Melanogaster* is Expressed in Neurogenic Territories and Encodes a Putative Transmembrane Protein with EGF–Like Repeats," *EMBO J.*, 6(11):3431–3440 (1987).

Wharton et al., "Nucleotide Sequence from the Neurogenic Locus Notch Implies a Gene Product that Shares Homology with Proteins Containing EGF–Like Repeats," *Cell*, 43:567–581 (Dec., 1985).

Wilkinson et al., "A Molecular Analysis of Mouse Development from 8 to 10 Days Post Coitum Detects Changes Only in Embryonic Globin Expression," *Development*, 99:493–500 (1987).

Williams and Barclay, "The Immunoglobulin Superfamily–Domains for Cell Surface Recognition," *Ann Rev. Immunol.,* 6:381–405 (1988).

Ylänne et al., "Platelet Glycoprotein IIb/IIIa Complex in Cultured Cells. Localization in Focal Adhesion Sites in Spreading HEL Cells," *Blood,* 72(5):1478–1486 (Nov., 1988).

Yochem et al., "The *Caenorhabditis elegans lin–12* Gene Encodes a Transmembrane Protein with Overall Similarity to *Drosophila Notch,*" *Nature,* 335:547–550 (Oct. 6, 1988).

Partanen et al, "A Novel Endothelial Cell Surface Receptor Tyrosine Kinase with Extracellular Epidermal Growth Factor Homology Domains" *Mol. and Cell Biol.* vol. 12, p. 1698–1707, 1992.

Korhonen et al, "Enhanced Expression of the tie Receptor Tyrosine Kinase in Endothelial Cells During Neovascularization" Blood, vol. 80, p. 2548–2555, 1992.

Folkman and Klagsbrun, "Angiogenic Factors," *Science,* 235:442–447 (Jan. 23, 1987).

Greenwood and Hunter, "The Preparation of I–Labelled Human Growth Hormone of High Specific Radioactivity," *Biochem. J.* 89:114–123 (1963).

Harlow and Lane, *Antibodies: A Laboratory Manual,* pp. 139–244 (Cold Spring Harbor Laboratory) (1988).

Heldin and Westermark, "Platelet–derived growth factor: mechanism of action and possible in vivo function," *Cell Reg.,* 1:555–566 (Jul. 1990).

Hemmila et al., "Euporium as a Label in Time–Resolved Immunofluorometric Assays," *Anal. Biochem.,* 137:335–343 (1984).

Huang et al., "The Hematopoietic Growth Factor KL is Encoded by the SI Locus and is the Ligand of the c–kit Receptor, the Gene Product of the W Locus," *Cell,* 63:225–233, (Oct. 5, 1990).

Kettleborough et al., "Humanization of a Mouse Monoclonal Antibody of CDR–Grafting: the Importance of Framework Residues on Loop Conformation," *Protein Engineering,* 4(7):773–783 (1991).

Mather et al., "Reduction–Mediated Technetium–99m Labeling of Monoclonal Antibodies," *J. Nucl. Med.,* 31(5):692–697 (May 1990).

Mukkala et al., "The Synthesis and Use of Activated N–Benzyl Derivatives of Diethylenetriaminetetraacetic Acids: Alternative Reagents for Labeling of Antibodies with Metal Ions," *Anal. Biochem.,* 176:319–325 (1989).

Oikawa et al., "A Specific Heterotypic Cell Adhesion Activity between Members of Carcinoembryonic Antigen Family, W272 and NCA, Is Mediated by N–domains," *J. Biol. Chem.,* 266(13):7995–8001 (May 5, 1991).

Partanen et al. "A Novel Endothelial Cell Surface Receptor Tyrosine Kinase with Extracellular Epidermal Growth Factor Homology Domains," *Mol. Cell Biol.* 12(4):1698–1707 (Apr. 1992).

Press et al., "Treatment of Refractory Non–Hodgkin's Lymphoma with Radiolabeled MB–1 (Anti–CD37) Antibody," *J. Clin. Oncol.* 7(8):1027–1038 (Aug. 1989).

Schwartz et al., "A Novel Approach to Tc–99m–Labeled Monoclonal Antibodies," *J. Nuclear Medicine* 23(4):721 (Apr. 1987).

Sherr et al., "The C–fms Proto–oncogene Product is Related to the Receptor for the Mononuclear Phagocyte Growth Factor, CSF–1," *Cell,* 41:665–676 (Jul. 1985).

Tessier et al., "Enhanced secretion from insect cells of a foreign protein fused to the honeybee melittin signal peptide," *Gene,* 98:177–183 (1991).

Ullrich and Schlessinger, "Signal Transduction by Receptors with Tyrosine Kinase Activity," *Cell,* 61:203–212 (Apr. 20, 1990).

ANTIBODIES RECOGNIZING TIE RECEPTOR TYROSINE KINASE AND USES THEREOF

The present application is a continuation-in-part of International Application No. PCT/FI93/00006, filed Jan. 8, 1993, which in turn claims priority from U.S. patent application Ser. No. 07/817,800, filed Jan. 9, 1992, now abandoned. The present application also is a continuation-in-part of U.S. patent application Ser. No. 08/167,453, filed Dec. 15, 1993, now abandoned, which is a continuation of U.S. patent application Ser. No. 07/817,800, filed Jan. 9, 1992, now abandoned.

FIELD OF INVENTION

The present invention generally relates to antibodies which are reactive with Tie, a receptor tyrosine kinase found in various endothelial cells and in certain tumor cell populations. In addition, the present invention relates to methods for making such antibodies and to methods of their use.

BACKGROUND OF INVENTION

Cardiovascular diseases and cancer are very common in Western countries and these disease groups are economically important because patients suffering from them typically lose large amounts of work time and must be treated for prolonged periods. Blood vessels play an important role in the evolution of cardiovascular diseases, as well as in the pathogenesis of cancer. A central role in the pathogenesis of vascular diseases is played by endothelial cells lining the inner walls of blood vessels. Traumas and metabolic disturbances in endothelial cells give rise to so-called atheroma plaques and to arteriosclerosis. Neovascularization, induced by tumor cells via growth factors stimulating endothelial cells, is an important event in various cancers. It is known from experimental investigations that in order to develop and grow, cancer cells need neovascularization to ensure transport of nutrients and oxygen into the growing tissue.

The cellular behavior responsible for the development, maintenance, and repair of differentiated cells and tissues is regulated, in large part, by intercellular signals conveyed via growth factors and similar ligands and their receptors. The receptors are located on the surface of responding cells and they bind peptide or polypeptide growth factors, as well as other hormone-like ligands. As a result of this interaction, rapid biochemical changes occur in the responding cells which lead to a rapid and a long-term readjustment of cellular gene expression. Several receptors associated with various cell surfaces may bind specific growth factors.

Tyrosine phosphorylation is one of the key modes of signal transduction across the plasma membrane. Several currently-known protein tyrosine kinase genes encode transmembrane receptors for polypeptide growth factors and hormones, such as epidermal growth factor (EGF), insulin, insulin-like growth factor (IGF-I), platelet derived growth factors (PDGF-AA, AB and BB), and fibroblast growth factors (FGFs). See e.g., Heldin et al., *Cell Reg.,* 1:555–556 (1990); Ullrich, et al., *Cell,* 61:2243–354, (1990). Endothelial cells growth factor receptors are of particular interest due to the possible involvement of growth factors, such as FGFs, in several important physiological and pathological processes including angiogenesis, arteriosclerosis and inflammatory diseases (Folkman, et al., *Science,* 235:442–447, 1987). Also, the receptors of several hematopoietic growth factors are tyrosine kinases. These include the colony stimulating factor 1 receptor (Sherr et al., *Cell,* 41:665–676, 1985) and c-kit, the stem cell factor receptor (Huang et al., *Cell,* 63:225–233, 1990).

The receptor tyrosine kinases may be divided into evolutionary subfamilies, on basis of structural similarities and differences, these proteins differ in their specificity and affinity (Ullrich et al., supra). In general, receptor tyrosine kinases are glycoproteins which comprise an extracellular domain, capable of binding the growth factor, a transmembrane domain, which usually is an α-helical portion of the protein, a juxtamembrane domain, where the receptor may be regulated by, e.g., protein phosphorylation, a tyrosine kinase domain, which is the enzymatic component of the receptor and a carboxy terminal tail, which, in many receptors, is involved in recognition and binding of specific substrates.

Recently, a novel endothelial cell receptor tyrosine kinase, called Tie, has been described in co-owned International Patent Publication WO 93/14124. Tie is an acronym corresponding to tyrosine kinase containing immunoglobulin- and EGF-like domains. Tie is useful in the diagnosis and treatment of certain diseases involving endothelial cells and their associated Tie-receptors, such as neoplastic diseases involving tumor angiogenesis, wound healing, thromboembolic diseases, atherosclerosis, and inflammatory diseases.

SUMMARY OF THE INVENTION

It is an object of the present invention to provide diagnostic methods for monitoring endothelial cells in tissue samples and in whole organisms. It is a further object of the present invention to provide clinical detection methods describing the state of endothelial cells (traumas, growth, etc.) and methods for detecting endothelial cells and thus vascular growth in an organism. The present invention provides antibodies recognizing Tie. In a preferred embodiment, antibodies of the invention are directed against extracellular portions of Tie. Also in a preferred embodiment, the invention provides a monoclonal antibody designated 3C4C7G6. The hybridoma cell line which produces monoclonal antibody 3C4C7G6 was deposited with Deutsche Sammlung von Mikroorganismen und Zellkulturen GmbH (DSM) Mascheroder Weg 1b, D-38124 Braunschweig on Dec. 2, 1993, under the provisions of the Budapest Treaty (DSM accession number ACC2159).

Monoclonal antibodies labeled with a detectable marker are also provided. As used herein, the term detectable marker encompasses any detectable marker known to those skilled in the art. However, in a preferred embodiment of this invention, the detectable marker is selected form the group consisting of radioisotopes, dyes, enzymes and biotin. For the purpose of this invention suitable radioisotopes include, but are not limited to, $^{125}$I and $^{131}$I.

The present invention also provides monoclonal antibodies conjugated to an imageable agent. As used herein, the term imageable agent includes, but is not limited to, radioisotopes. A preferred radioisotope is technetium-$^{99}$m.

The present invention further provides a method for detecting and identifying human tissues undergoing neovascularization, which method comprises the steps of contacting a sample suspected of undergoing neovascularization with a Tie-specific monoclonal antibody under conditions suitable for forming a complex between the monoclonal antibody and the antigen, and detecting the presence of any complex formed. A tissue which may be detected by this method is any normal, precancerous or cancerous solid tumor tissue with Tie-containing endothelial cells or leukemia cells which express the Tie-receptor. In one embodiment of the present invention, the monoclonal antibody is labeled with a detectable marker as described herein. Methods of the invention are useful for detecting and differentiating various forms of cancer.

Monoclonal antibodies of the present invention may also be used in a method for detecting the presence of Tie-receptors in a cell sample, comprising the steps of exposing a cell sample to a monoclonal antibody of the present invention; and detecting the binding of said monoclonal antibody to Tie-receptors.

The exposure of a cell mixture to such monoclonal antibodies may be in solution, as is the case for fluorescence-activated cell sorting, or it may be on solid tissue specimens, such as biopsy material, or it may be with the monoclonal antibody immobilized on a solid support, as is the case with column chromatography or direct immune adherence. The mixture of cells that is to be exposed to the monoclonal antibody may be any solution of blood cells or tissue cells. Preferably, the cell mixture is from normal mammalian cells, mammalian bone marrow, circulating blood, or suspected tumor tissue, more preferably normal cells, leukemia cells and solid tumor cells. After exposure of a cell mixture to monoclonal antibody, those cells with Tie-receptors bind to the monoclonal antibody to form an antibody-Tie-receptor complex. The presence of the antibody-Tie-receptor complex, and therefore Tie-receptors, is detected by methods known in the art. Such methods include ELISA, immunohistochemistry, RIA using an $^{125}$I-label, and autoradiography.

A method for imaging the presence of angiogenesis in wound healing, in inflammations, or in tumor of human patients, is also provided by the present invention. Methods comprise administration of labeled antibodies and detection by imaging at sites where endothelial cells are engaged in formation of new blood vessels.

Humanized monoclonal antibodies of the present invention are useful in treating neoplastic diseases involving endothelial cells with associated Tie-receptors, by administration of therapeutically-effective amounts of an anti-neoplastic therapeutic agent conjugated to such a monoclonal antibody to patients suffering from such diseases. A therapeutically-effective amount of a therapeutic agent is any amount of the agent that will cause inhibition of growth of the tumor, preferably causing death of the neoplastic cells and a decrease in the total number of neoplastic cells in an organism. Examples of such therapeutic agents include antibodies coupled to radioisotopes, such as 90Y or to toxin conjugates such as ricin and different microbial toxins.

Conjugation of a therapeutic agent to the monoclonal antibody may be accomplished using known techniques as described in e.g., Press et al., *J. Clin. Oncol.* 7:1027–1038 (1989). Preferably, the conjugation site on the monoclonal antibody is at a location distinct from the binding site for the monoclonal antibody to the Tie-receptor. It is also preferred that the conjugation site on the therapeutic agent be at a functional group distinct from the active site of the therapeutic agent. More preferably, the conjugation site will also be situated so as to minimize conformational changes of the monoclonal antibody or the therapeutic agent.

The present invention also relates to a method for treating neoplastic diseases comprising administration of a therapeutically effective amount of a therapeutic agent conjugated to a binding fragment of a monoclonal antibody of the present invention. Suitable binding fragments are those fragments which retain sufficient size and structure to allow binding of the fragment to the Tie-receptor. Such fragments may be prepared by numerous methods known in the art. The prepared binding fragments may be assayed for ability to bind to the Tie-receptor using the binding assays described in Example 5.

Administration of monoclonal antibodies of the present invention involves administration of an appropriate amount of a pharmaceutical composition containing the monoclonal antibodies as an active ingredient. In addition to the active ingredient, the pharmaceutical composition may also include appropriate buffers, diluents and additives. Appropriate buffers include Tris-HCl, acetate, glycine and phosphate, and preferably phosphate at pH 6.5 to 7.5. Appropriate diluents include sterile aqueous solutions adjusted to isotonicity with NaCl, lactose or mannitol, and preferably NaCl. Appropriate additives include albumin or helartin to prevent adsorption to surfaces, detergents (e.g., Tween 20, Tween 80), solubilizing agents (e.g., glycerol, polyethylene glycol), antioxidants (e.g., ascorbic acid, sodium metabisulfite), and preservatives (e.g., Thimerosal, benzyl alcohol, parabens).

Administration may be by any conventional means including intravenous, subcutaneous or intramuscular administration. The preferred route of administration is intravenous. Administration may be a single dose or may occur in an appropriate number of divided doses.

Preferably, the pharmaceutical preparation is in unit dosage form. In such form, the preparation is subdivided into unit doses containing the appropriate quantities of the active component, e.g., an effective amount to achieve the desired purpose.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered essentially continuously or in portions during the day if desired. The amount and frequency of administration will be regulated according to the judgment of the attending clinician considering such factors as age, condition and size of the patient as well as severity of the disease being treated.

A typical recommended dosage regime for use in the present invention is from about 0.1 to about 10 mg active ingredient per day.

The development and use of mouse monoclonal antibodies as therapeutic agents suffers from the fact, that the half life is reduced due to the formation of human anti-mouse antibody response (HAMA). Therefore the efficacy of the mouse monoclonal antibodies in patients is lower (review by Adair et al., 1990). Also adverse side-effects occur when repeated administrations of foreign proteins are used. Many of these problems can be solved using human monoclonal antibodies. At present these antibodies can be generated from mouse monoclonal antibodies using molecular biology techniques, where the complementary determining region (CDR) of mouse mAbs are joined with human mAbs. These humanized antibodies are suitable for use in immunotherapy in humans. Also single chain antibodies (scFv) will be constructed. In constructing these scFv's different lengths of linker sequences will be used as described by Whitlow et al. (1993) in order to optimize the binding of the antibody to the antigen.

As is evident from the foregoing, antibodies according to the present invention are useful in the diagnosis and identification of diseases states (e.g., various types of cancer), the detection and monitoring of wound healing, the treatment of various neoplastic diseases, and prophylaxis. Other uses of the presently-claimed subject matter are apparent to the skilled artisan.

DETAILED DESCRIPTION OF THE INVENTION

Figure 1A:
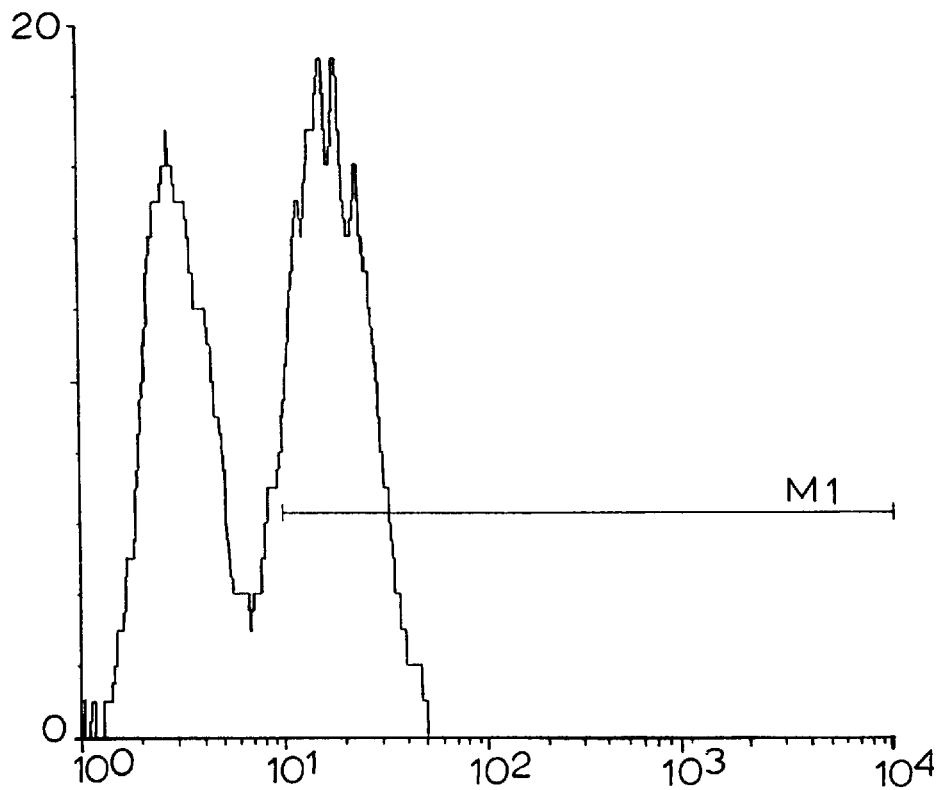
FIG. 1 represents an analysis of MOLT-4 and HEL cells by immunofluorescence for Tie and flow cytometry.

The following examples are provided to illustrate specific embodiments of the present invention, without limiting the scope thereof. Other uses and embodiments of the present invention are readily appreciated by one of ordinary skill in the art.

EXAMPLE 1

Production of the Extracellular Domain of Tie in a Baculovirus Expression System The cDNA sequence of the Tie protein has been disclosed in Partanen J., et al., *Mol. Cell Biol.* 12:1698–1707, (1992), incorporated by reference herein. The tie cDNA (SEQ ID NO: 4) sequence encodes an open reading frame of 1138 amino acids (SEQ ID NO: 5). The translational initiator (methionine) is followed by a hydrophobic amino acid sequence characteristic of signal sequences for translocation into the endoplasmic reticulum.

Beginning with amino acid residue 214 of the tie open reading frame, there is a region of 130 amino acid residues containing 24 cysteine residues altogether. This region can be aligned into three repeated EGF-like homologous domains containing eight cysteine residues each.

The most amino-terminal region of the tie extracellular domain shows weak but significant homology to the amino terminus of chicken N-CAM protein. (Cunningham et al, *Science*, 236:799–806 (1987).) As in N-CAM, a pair of cysteine residues surrounded by consensus motifs characteristic for the proteins of the Ig superfamily is found in this region. In addition, two pairs of cysteine residues are located on the carboxyl-terminal side of the three EGF repeats. The amino acid sequence around the first cysteine pair shows additional homology to Ig domains.

The extracellular region following the Ig2 domain can be aligned into three segments that are homologous to fibronectin type III repeats. Five consensus sites for potential N-linked glycosylation (NXS/T, where X=any amino acid) can be distinguished in the extracellular domain.

Amino acid residues 761–786 (SEQ ID NO: 5) form a hydrophobic stretch of sequence, which is likely to function as the transmembrane domain of the receptor, followed by several basic residues on the putative cytoplasmic side of the polypeptide. The juxtamembrane domain is 50 residues long before the beginning of tyrosine kinase sequence homology at amino acid 837. With the interruption of homology in the kinase insert sequence of 14 amino acids (SEQ ID NO: 5, residues 938–951), this homology is first lost at the beginning of the 31 amino-acid carboxyl-terminal tail of the receptor (residues 1108–1138). The cDNA sequence encoding the extracellular domain of Tie (amino acids 24–760) was PCR amplified and cloned into the BamHI site of pVT-Bac vector (Tessier et al., *Gene,* 98:177–183, 1991) using PCR primers 5'-cgtagatctggcggtggacctgac-3', (SEQ ID NO: 1) and 5'-ggccatgatcactagtgatggtgatggtgatgctgctgatcc-aggccctcttcagc-3' (SEQ ID NO: 2). A sequence encoding a Factor X cleavage site (IEGR) followed by six consecutive histidine residues (SEQ ID NO:3) was inserted at the 3' end of the cDNA. The resulting vector, designated pVT-Tie, was then transfected into insect cells for expression of the Tie extracellular domain.

The pVT-Tie vector was co-transfected with Baculo Gold baculovirus DNA (Pharmingen Cat. 21100D) into SF-9 insect cells. Viral isolates were purified by plaque assay in agarose from the conditioned medium (TNMFH+5% FCS) of the transfected cells and were tested for expression of the recombinant protein in High- Five insect cells (Invitrogen). One of the isolates (BG-3 virus) was chosen for large scale protein production.

High Five cells were infected with the BG-3 virus and the conditioned medium (EX-CELL 400, JRH Scientific) of the infected cells was collected after two days. The recombinant BG-3 protein was purified from the medium by ConA affinity chromatography.

EXAMPLE 2

Production of Anti-Tie Monoclonal Antibodies in Balb/c Mice (Anti-BG-3 3C4C7G6)

Three month old Balb/c female mice were immunized by intraperitoneal injection of the recombinant-produced BG-3 protein (50 µg/mouse) emulsified with Freund's complete adjuvant. Booster injections of 50 µg were given at three-to-four week intervals and a final booster (20 µg BG-3 in PBS administered intravenously) was given after another three-week interval. Four days after the final booster dose, the mice were sacrificed and mouse splenic lymphoid cells were fused with SP 2/0 plasmacytoma cells at a 2:1 ratio, respectively. The fused cells were harvested in 96-well culture plates (Nunc) in Ex-Cell 320 medium (Seralab) containing fetal calf serum (FCS, 20%) and HAT supplement (hypoxanthine-aminopterin-thymidine, Gibco, 043-01060H, diluted 50-fold). Cells were cultured at +37° C., in a 5% $CO_2$ atmosphere. After 10 days, HAT-supplemented medium was changed to HT-supplemented cell culture medium (Gibco, 043-01065H, diluted 50-fold). HT medium was identical to HAT medium but without aminopterin.

Two to three weeks after fusion, specific antibody production was determined by the antigen-specific immunofluorometric assay, IFMA, described in Example 5. The master clones were cloned by limited dilutions (Staszewski, 1984). Positive clones were expanded onto 24-well tissue culture plates (Nunc), recloned, and retested by the same method. Positive clones were tested by fluorescence-activated cell sorting (FACS). The stable clone secreted immunoglobulins belonging to the IgG class. That clone, designated 3C4C7G6, was found to stably secrete monoclonal antibody which was determined to be of immunoglobulin class IgG1 by IFMA. Hybridoma 3C4C7G6 was deposited with the German Collection of Microorganisms and Cell Cultures, Department of Human and Animal Cell Cultures, Mascheroder Weg 1b, 38124 Braunschweig, Germany, Dec. 2, 1993, and given accession No. ACC2159.

Balb/c mice were used to produce monoclonal antibodies in ascites fluid. The hybridomas described above were intraperitoneally (i.p.) injected into mice after pretreatment of the animals with pristine (2,6,10,14-tetramethylpentadecan 98%, Aldrich-Chemie D-7924 Steinheim, cat.no T 2,280-2). 0.5 ml of pristine (i.p.) was injected about two weeks prior to the injection of the hybridoma cells. The amounts of cells injected were approximately 7.5 to $9 \times 10^6$ per mouse. The resultant ascites was collected 10–14 days after injection of the hybridomas and contained, on average, 0.3 mg/ml of antibody as determined by antigen specific IFMA as described in Example 5. Additional means of producing monoclonal antibodies are known to the skilled artisan and may be found, inter alia, in Harlow, et al. (eds.), *Antibodies: A Laboratory Manual*, 139–244 (1988), incorporated by reference herein.

EXAMPLE 3

Large Scale In-Vitro Production of Anti-Tie Monoclonal Antibody 3C4C7G6 in Hollow Fiber Bioreactors Monoclonal antibodies against Tie were produced in vitro using the Technomouse System (Tecnorama) according to the manufacturer's instruction. Media bottles with caps and filters were first autoclaved at 121° C. and 1.1 bar pressure for half an hour. They were then filled with 1 L Dulbecco's MEM (1:10 Gibco, 042-02501, with glucose 4.5 g/L, glutamine 2 mmol/L 066-1051H, Na-pyruvate 1 mmol/L 066-1840E). The bioreactor holder was aseptically transferred in the Technomouse tray. The pump was loaded, and the medium lines as well as the empty waste bottles (the outflow line) aseptically connected.

The fill and flush program was performed according to the manufacturer's instructions to wash preservative from the Intracapillary space (IC) of the bioreactor. The program was started at a flow rate of 150 ml/h for 4 hours. The washing was continued at a flow rate of 50 ml/h for 20 hours with simultaneous washing of the Extracapillary (EC) space with 5% FCS in Dulbecco's MEM (DMEM). Medium in the EC space was aseptically changed to fresh medium. One day later the Bioreactor was ready for inoculation of the hybridoma cells.

Hybridoma cells were harvested in cell culture bottles in 10% FCS-DMEM and $72 \times 10^6$ cells were collected and inoculated in 5 ml volume of DMEM containing 5% FCS. The medium flow rate in the intracapillary space was 100 ml/h. A recycling method was used for harvesting monoclonal antibodies as follows: a medium line was connected to the medium bottle "out", taking the medium out from the bottle to the Bioreactor intra-capillary space; the outflow line was connected to the medium bottle "in" bringing the medium back to the bottle. Monoclonal antibodies were harvested three times a week on Monday, Wednesday, and Friday, and a 10 ml volume of fresh medium containing 2.5% FCS in DMEM was replaced each time.

The anti-BG-3 cell line, 3C4C7G6, produced antibodies at a mean concentration of 152 µg/ml in the cell culture medium. After inoculation of the cells to the Bioreactor in the Technomouse system ($72 \times 10^6$ cells), the antibodies produced were harvested in a two-to-three day period. The mean production was 4.5 mg/week and the cumulative production over 2 months was 37 mg.

The antibody produced in either ascites fluid or in the Technomouse-system was purified using an Affigel Protein A MAPS II Kit (BioRad) according to the manufacturer's instruction. The column was equilibrated for the purification procedure with binding buffer (pH 9.0). The antibodies from ascites fluid were connected to the protein A-matrix in the binding buffer and the unbound material was washed with the binding buffer (detected at 280 nm by UV-spectrometry). The specifically-bound material was eluted from protein-A with elution buffer at pH 3.0 and the fractions were collected in the tubes containing the volume of 1 mol/L Tris-HCl pH 9.0, which was needed to neutralize the fraction immediately. The column was regenerated with regeneration buffer and stored until next use in 50 mmol/L Na-phosphate buffer pH 7.5 containing 0.05% $NaN_3$ as preservative.

EXAMPLE 4

Labelling of Tie-Protein with Europium

The extracellular domain of Tie disclosed in Example 1 (BG-3) was labeled for use in assays. The labelling was performed according to Mukkala et al., *Anal.Biochem.*, 176 (2): 319–325 1989, with modifications as follows: a 125 times molar excess of isothiocyanate DTTA-Eu (N1 chelate, Wallac, Finland) was added to BG-3 solution (0.5 mg/ml in 50 mmol/L borate buffer, pH 8.6) and the pH was adjusted to 9.8 by adding one tenth of 0.5 mol/L sodium carbonate (Merck) buffer, pH 9.8. The labelling was performed overnight at +4° C. Unbound label was removed using PD-10 (Pharmacia, Sweden) with TSA buffer (50 mmol/L Tris-HCl pH 7.8 containing 0.15 mol/L NaCl) as eluent.

After purification, 1 mg/ml bovine serum albumin (BSA) was added to the labeled BG-3 and the label was stored at +4° C.

The number of Europium ions incorporated per BG-3 molecule was 2.9, as determined by measuring the fluorescence in a ratio to that of known $EuCl_3$ standards (Hemmila et al., *Anal.Biochem.*, 137:335–343 (1984).

EXAMPLE 5

Immunofluorometric Screening Assay (IFMA)

Antibodies produced against the Tie-receptor were screened using a sandwich-type immunofluorometric assay using microtitration strip wells (Nunc, polysorb) coated with rabbit antimouse Ig (Z 259, Dakopatts). The precoated wells were washed once by Platewash 1296-024 (Wallac) with wash solution (DELFIA). The DELFIA assay buffer was used as a dilution buffer for cell culture supernatants and for serum of the splenectomized mouse (at dilutions between 1:1000 to 1:100,000) used as positive control in the preliminary screening assays.

AntiBG-3 3C4C7G6 produced as ascitic fluid and purified with Affigel Protein A MAPS was used as a standard in the later assays at a concentration between 0.25 ng/ml and 60 ng/ml in assay buffer (100 ul, DELFIA).

An incubation for 2 hours at room temperature (or alternatively an overnight incubation at +4° C.) was begun by shaking on a Plateshake shaker (1296-001, Wallac) for 5 minutes followed by washing four times with wash solution as described above.

The Europium-labeled BG-3 prepared in Example 4 was added at a concentration of 10 ng/well in 100 µl of the assay buffer. After 5 minutes on a Plateshake shaker and one hour incubation at room temperature, the strips were washed as described above.

Enhancement solution (DELFIA) was added at 200 µl /well. The plates were then shaken for 5 minutes on a Plateshake shaker and the intensity of fluorescence was measured by ARCUS-1230 (Wallac) in 10 to 15 minutes (Lovgren et al., In: Collins W. P. (ed), Alternative Immunoassays, John Wiley & Sons Ltd, 1985; 203–216).

Figure 2:
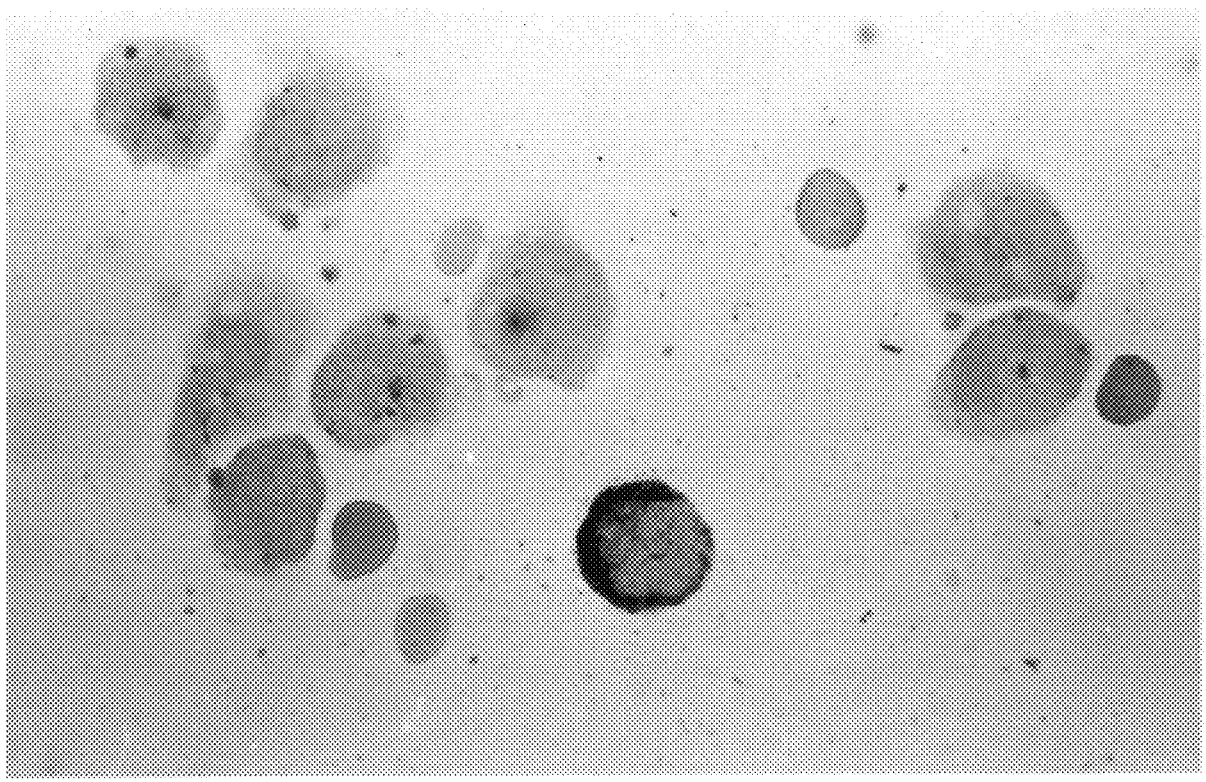
FIG. 2 shows immunoperoxidase staining of Tie in human blood cells.

The sandwich-type DELFIA is very sensitive, the theoretical sensitivity being below 0.25 ng/ml for this anti-Tie monoclonal antibody. Although the sensitivity was convenient for quantitation of Mabs produced in cell culture supernatants the assay was also practical for quantitation of Mabs produced in vitro. The linear range reached from 0.25 ng/ml to 60 ng/ml (FIG. 2). Intra assay variation was found to be very low.

EXAMPLE 6

Radiolabeling of Monoclonal Antibody 3C4C7G6 for In-Vivo Detectin of Tie-Receptor The anti-BG-3 monoclonal antibody, 3C4C7G6, was labeled with $^{125}$I using the chloramine-T method of Greenwood et al., *Biochem. J.* 89:114–123 (1963). Na$^{125}$I (1 mCi) was used to label 40 µg antibody. Labeled antibody was purified by eluting with Sephadex-G25 resulting in a main fraction of 1.8 ml.

$^{125}$I-labeled anti-BG-3 (3C4C7G6 ) was administered intravenously in doses of either 1.2 µg or 2.4 µg to Lewis-lung-carcinoma bearing mice. The biodistribution of the labeled antibody in mice was measured at five different time points: at 6 h (N=4), at 24 h (N=7), at 47 h (N=5), at 70 h (N=3) and at 117 h (N=2). Tissue was washed with 0.9% NaCl, weighed, and activity was measured with a gamma counter. The results are shown in Table I for the various tissue samples measured.

TABLE 1

BIODISTRIBUTION TO TISSUES AT TIME POINTS 1–5

|  | % ID/g 6 h | % ID/g 24 h | % ID/g 47 h | % ID/g 70 h | % ID/g 117 h |
| --- | --- | --- | --- | --- | --- |
| blood | 36,22871 | 11,26086 | 9,343041 | 7,87285 | 2,749225 |
| heart | 7,828641 | 2,842418 | 1,932395 | 1,391288 | 0,548053 |
| aorta | 16,07039 | 5,553582 | 3,707159 | 3,166192 | 0,798207 |
| lung | 9,091084 | 3,823566 | 3,087934 | 2,555693 | 0,987308 |
| liver | 6,940821 | 2,355467 | 1,770392 | 1,568976 | 0,685282 |
| kidney | 9,331627 | 3,490624 | 2,556933 | 1,809169 | 0,802883 |
| brain | 0,548253 | 0,228239 | 0,149502 | 0,146163 | 0,042287 |
| blood vessels | 22,64432 | 4,712374 | 2,435758 | 2,65011 | 0,485038 |
| tumor | 7,151142 | 3,620555 | 3,155919 | 2,179194 | 0,901169 |
| spleen | 5,840843 | 2,004754 | 1,396837 | 1,195612 | 0,622342 |
| bladder | 6,889924 | 4,36051 | 3,628196 | 3,523912 | 0,899099 |
| ovaries | 8,445497 | 3,617958 | 2,622101 | 2,387713 | 0,662774 |

The results show that anti-BG-3 activity was concentrated in blood, tumor, bladder, and blood vessels, and in some amount in lungs and ovaries. Activity in blood was high at the 48 and 70 hour time points: 9.3% ID/g and 7.9% ID/g (percentage of injected dose per gram of tissue normalized to a 20 g mouse). Anti-Bg-3 activity in blood was 11.3% at 24 hours and 36.2% at 6 hours time point.

Figure 3:
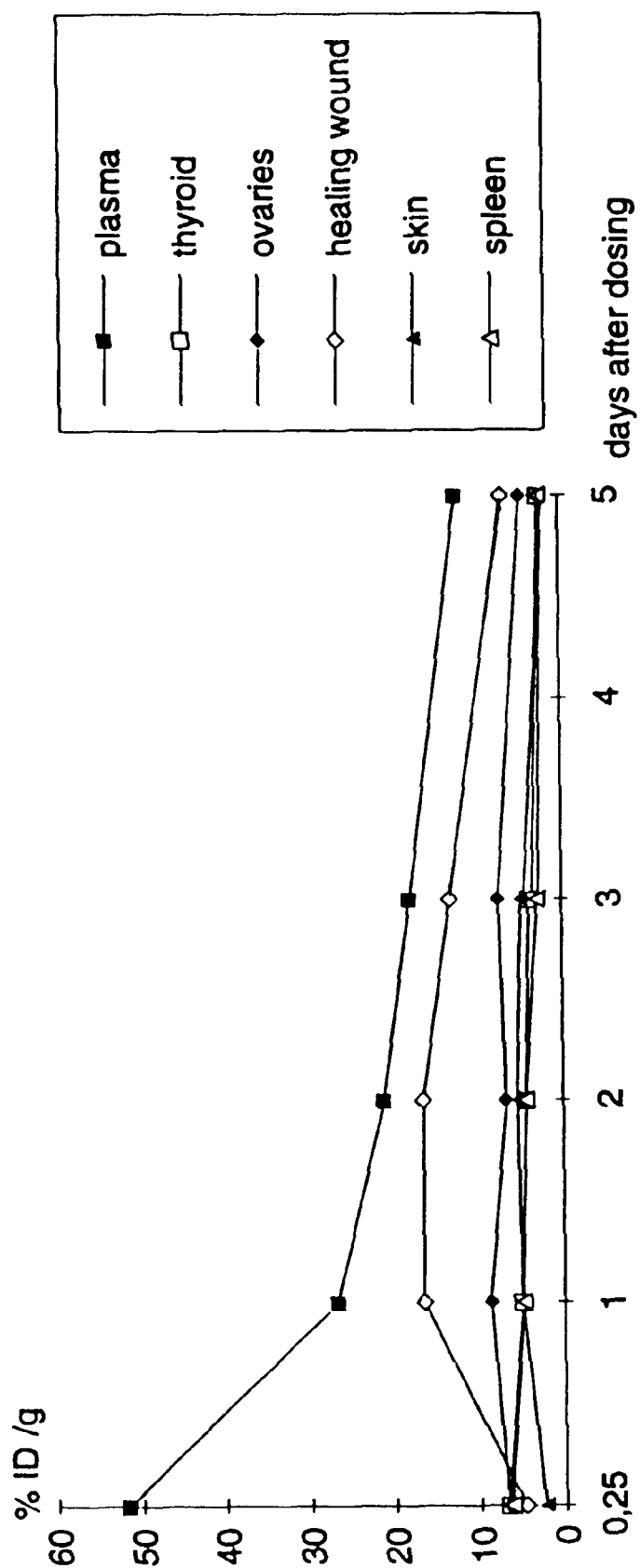
FIG. 3 shows the biodistribution of $^{125}$I-labelled monoclonal antibody 3C4C7G6 to selected target tissue in mice having an 8 day-old wound.

$^{125}$I-labelled anti-BG-3 (3C4C7G6) was also administered to mice having an 8 day-old wound in the skin epithelium ("wound healing mice"). The dose of antibody given to wound healing mice was 0.03 µg per animal. The biodistribution of antibody activity is shown in FIG. 3. In that Figure, the Y-axis represents the percent of injected dose (% ID/g) and the X-axis represents various time points of injection: 4 h (N=2); 24 h (N=6); 48 h (N=6); 72 h (N=4); and 120 h (N=4). The equilibrium established between target and plasma is also shown in the Figure.

EXAMPLE 7

TC-$^{99}$M-Labelling of Anti-Tie Monoclonal Antibodies for Imaging Studies

Anti-tie monoclonal antibody was labeled with technetium-$^{99}$m ("$^{99}$mTc") using the technique of Schwarz et al., *J.Nucl.Med.*, 28:721,1987, and Mather et al., *J.Nucl.Med.*, 31:692–697 (1990) incorporated by reference herein. 2-Mercaptoethanol (ME) was used to open the disulfide bonds of the heavy chain in the hinge region of the immunoglobulin. Antibody was concentrated to approximately 10 mg/L and sufficient ME was added to the antibody solution to provide a molar ratio of 1000:1 (0.47 µl ME/1 mg antibody). The mixture was incubated at room temperature for 30 minutes and the reduced antibody purified by gel filtration on a 20 ml Sephadex-G-50 column and eluted using phosphate-buffered saline as the mobile phase. The antibody fraction was pooled after measurement of optical density at 280 nm and stored at −20° C. as 0.5 mg aliquots for labelling with $^{99}$mTc.

Upon labelling with $^{99}$mTc, the antibody aliquot was thawed and reconstituted using a methylene diphosphonate (MDP) bone imaging kit (Amerscan Medronate II Technetium Bone Agent, N.165) with 5 ml 0.9% sterile saline according to the manufacturer's instructions. 35 µl of the MDP solution, containing 35 µg MDP and 2.4 µg SnF$_2$, was added to antibody aliquot and mixed well. $^{99}$mTc pertechnetate was added to the mixture which was shaken gently. The reaction was completed in 10 min. The radiochemical purity was measured by high pressure liquid chromatography.

Labelling of the reduced antibody gives a stabile $^{99}$mTc-labeled immunoglobulin because the unspecific binding of label is at minimum. The labelling efficiency is assessed by thin layer chromatography developed in 0.9% saline. The immunoreactivity is retained to not less than 85%. The in vivo stability will be analyzed by cysteine challenge assay in vitro.

Anti-Tie-antibodies labeled with $^{99}$mTc may be detected with an ordinary gamma-camera or with SPECT (Single Photon Emission Computerized Tomography) to visualize the flow rate of antibody in a human body.

EXAMPLE 8

Specificity of Anti-Tie Antibodies in Recognizing Tie Protein

A. Immunoprecipitation

The rabbit polyclonal and mouse monoclonal anti-Tie antibodies were used in the detection of the Tie protein from human leukemia cell lines and umbilical vein endothelial cells grown in vitro.

Immunoprecipitation of Tie was followed by Western immunoblotting using anti-Tie monoclonal antibodies directed against the GST-Tie2 protein expressed in bacteria. The GST-TIE2 protein was prepared as follows. A BAMHI-BAMHI fragment of Tie cDNA (nucleotides 520–1087) was subcloned into the BAMHI site of a pGEX1LambdaT vector (pharmacia), resulting in an open reading frame encoding glutathione-s-transferase fused to a region encoding amino acids 162–350 of the Tie protein. That construct was transformed into an *E. coli* DH5alpha strain and expression of the fusion protein was induced by IPTG. The resulting 40 kDa fusion protein was purified using a denaturing agarose gel (FMC) and was then used to immunize rabbits.

Production of antiserum against the carboxy terminus of the Tie protein was carried out by immunoprecipitation of Tie using rabbit antiserum against the carboxy-terminal 15 amino acids of Tie. Antisera were obtained by immunization with synthetic Tie coupled to keyhole limpet hemocyanin using glutaraldehyde.

Rabbits were immunized at biweekly intervals by intramuscular injections of 100–200 mg of antigen in a 1:1 emulsification with Freund's complete adjuvant following injection with antigen mixed with Freund's incomplete adjuvant. Antiserum was generally obtained after the second booster injection. In some cases immunoprecipitates of [$^{35}$S]-methionine-labeled Tie were used. The immunoprecipitates were analyzed by polyacrylamide gel electrophoresis and autoradiography.

The results show that rabbit antisera against the carboxyl terminal 15 amino acids of Tie may be used to specifically immunoprecipitate Tie from human cells expressing the Tie mRNA. Control precipitations with preimmune serum and antigen-blocked antibodies were negative. Furthermore, the anti-Tie monoclonal antibodies may be used to diagnose Tie expression by Western immunoblotting. After two subclonings, eight clones against the GST-Tie2 protein were obtained which reacted about equally well with Tie in Western immunoblotting.

B. Fluorescence Activated Cell Sorting

HEL-cells (Human Erythroleukemia cells, which co-express erythroid and megakaryocyte markers) were used for indirect immunofluorescence staining of Tie using the monoclonal antibodies generated above and FACS analysis. Cells were counted, washed, incubated in the presence of several dilutions of the antibodies (from 1:1 to 1:200), washed again, and then incubated in the presence of FITC-conjugated antibodies against mouse immunoglobulins (secondary antibodies). Analysis was done by FACS IV. As a negative control, cells were stained with nonspecific mouse immunoglobulins, followed by the same secondary antibodies as above. MOLT4 T-cell leukemia line which does not express Tie mRNA was used as a control cell line.

Figure 1B:
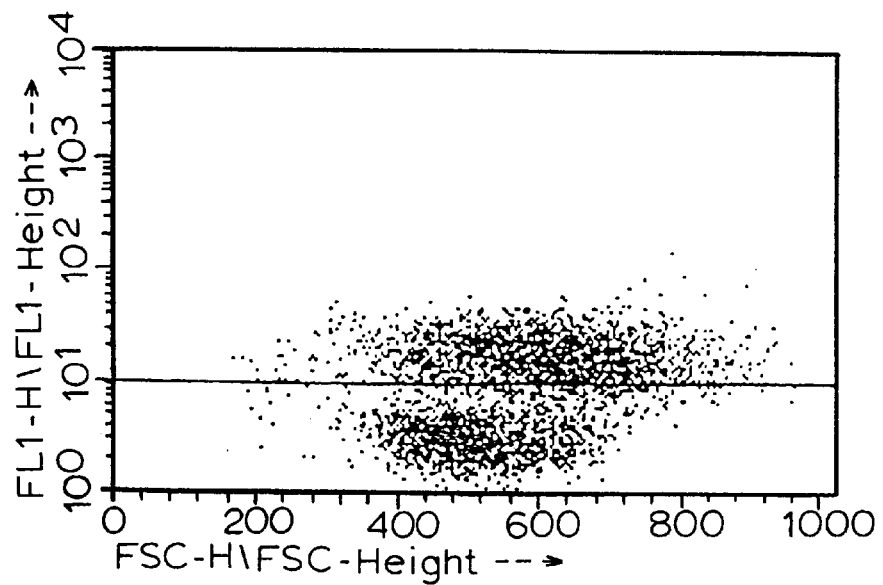

The results show that anti-Tie antibodies stain an average of 85% of HEL cells while less than 1% of MOLT cells stain positively for Tie. When cells from these two lines are mixed the antibodies discriminate positive HEL cells from negative MOLT cells (figure enclosed). From human bone marrow samples, about 0.6–0.9% of cells also positively stained with these antibodies. Cells from the human leukemia cell lines MOLT4 (a malignant T-cell line, which is Tie mRNA negative) and HEL (Human Erythroleukemia cell line, Tie mRNA positive) were mixed in suspension at approximately 1:1 ratio. The cells were then stained in suspension using the 3C4C7F6 monoclonal Tie antibodies diluted 1:10 and FITC conjugated anti-mouse IgG as the secondary antibody. As a negative control, normal mouse serum was substituted for the 3C4C7F6 monoclonal. Analysis was done using FACS IV. The results indicate two distinct cell populations, one Tie positive the other Tie negative, each comprising about 50% of the whole cell population analyzed (FIG. 1).

EXAMPLE 9

Humanization of Monoclonal Antibody 3C4C7G6

Monoclonal antibody 3C4C7G6 may be humanized using previously described methods (Kolbinger et al., 1993; Kettleborough et al., 1991). The humanization procedure involves incorporation of mouse kappa light (L) chain and heavy (H) chain complementarily determining regions (CDRs) into human variable (V) regions and making point mutations in human framework regions to preserve the original CDR conformations. The reshaped VL and VH chains are joined to DNAs encoding human kappa and gamma-1 constant regions, respectively, in suitable expression vectors.

The generation of Single-chain Fv regions (scFv) is accomplished as previously described by Whitlow et al. (1993).

The affinities of the humanized monoclonal antibodies and scFv's are tested using the methods described previously in this application.

EXAMPLE 10

Analysis of the Monoclonal Antibodies

The monoclonal cell culture supernatants were tested for their ability to recognize Tie-receptor on cell surfaces using FACS analysis. NIH3T3 cells transfected with Tie expression vector (full length Tie cDNA in pLTRpoly, Makela et al., 1991), control vector transfected NIH3T3 cells, as well as HEL cells (a human erythroleukemia cell line expressing endogenous Tie-receptor) and MOLT-4 cells (a human T-cell leukemia cell line not expressing Tie) were incubated with conditioned medium of different cell clones followed by FITC labeled rabbit-anti mouse antibodies (Dako). The labeled cells were analyzed by a fluorescence activated cell sorter (Beckton Dickinson).

TABLE 1

RESULTS OF ANTI-TIE EC MONOCLONALS (ANTI BG-3, 3C4C7G6)

| Clone | Slot Blot BG-3 | | | Western | FACS |
| --- | --- | --- | --- | --- | --- |
| | Delfia | media | denat. | | |
| 1H3F10 | +++ | +++ | +++ | (+) | − |
| H6 | +++ | +++ | +++ | (+) | − |
| H7 | +++ | +++ | +++ | (+) | + |
| 3C4C7 | +++ | +++ | + | − | ++ |
| E4 | +++ | ++ | (+) | − | + |
| G4 | +++ | ++ | (+) | − | + |
| 5C12G11 | +++ | +++ | +++ | − | − |
| H9 | +++ | +++ | +++ | (+) | − |
| 6A11A11 | ++ | ++ | + | − | + |
| H6 | ++ | ++ | (+) | − | + |
| H9 | ++ | ++ | + | − | + |
| 9B10E6 | + | ++ | +++ | − | − |
| G7 | + | ++ | +++ | − | − |
| 9E7E9 | +++ | +++ | +++ | (+) | − |
| E10 | +++ | ++ | ++ | (+) | − |
| H6 | +++ | ++ | ++ | (+) | − |

Ascites is also produced from the following clones: 1H3H7, 3C4C7, 5C12H9.

We have also produced monoclonals using GST-Tie fusion protein in immunizations. This fusion protein was produced in bacteria and it contains EGF-domains of the Tie-receptor. Ascites from anti GST-Tie2 4B2G4B12 and 4B2G4G8 have also been purified with protein-A column. Such preparations work well in Western blotting.

To mobilize hematopoietic stem cells into the peripheral blood, cyclophosphamide was given to a patient and buffy coat cells were collected from the peripheral blood seven days later. Red cells were hemolyzed from the cell suspension and cytocentrifuge slides prepared. These were then used for immunostaining using the purified Tie monoclonal antibody 3C4C7G6 and the immunoperoxidase method. Five positively staining cells were identified among the about 70,000 cells on a slide. (The dark staining of one positive cell in the figure is the result of the peroxidase reaction and identifies a Tie-positive cell). In analysis of bone marrow cells by double immunofluorescence staining, Tie-positive cells (less than 1 %) could not be assigned to a clear hematopoietic lineage. In immunoperoxidase staining the Tie-positive cells were small and round, with a large nucleus and scant cytoplasm (FIG. 2).

EXAMPLE 11

Conjugation of Tie Specific Monoclonal Antibody to a Therapeutic Agent

Monoclonal antibody 3C4C7G6, or humanized antibodies as described in Example 9, may be coupled or conjugated to a variety of agents, for diagnostic use, as described in Examples 6 and 7, or for therapeutic use of the resulting conjugate.

For use in therapy of tumors and of dispersed malignancies such as leukemias, the antibodies may be coupled to radioisotopes such as $^{32}P$, $^{131}I$, $^{125}I$, $^{90}Y$, $^{188}Re$, $^{212}Pb$, $^{212}Bi$ or $^{10}B$ (See e.g., Scheinberg et al., Oncology, 1:31–37, 1987). Conjugation of radioisotopes to the antibody is accomplished by direct attachment of the isotopes to the antibodies, by methods described in the art (See e.g., Schwartz J., *Nuclear Medicine* 28:721, 1987, incorporated by reference herein) or by the aid of chelate linkers, which bind the radioisotope to the antibody or by a secondary antibody to the specific antibody. A variety of other agents may be attached to the antibodies. Such agents include antitumor drugs and antibiotics which are toxic by way of interaction with DNA via intercalation (e.g., daunomycin, adriamycin, aclacinomycin) or cleavage of DNA (e.g., esperamycin, calicheamycin, neocarzinostatin) and other toxic cytostatic drugs such as cis-platinum, vinblastine and methotrexate (see e.g., Greenfield et al., *Antibody, Immunoconjugates and Radiopharmaceuticals*, 4:107–119, 1991). These agents are coupled by covalent attachment of appropriate derivatives of the agents.

Many proteins and glycoproteins are also available for use in therapeutic conjugates of the antibodies. These include bacterial toxins such as Diphtheria toxin, Shigella toxin, and Pseudomonas exotoxin; plant toxins, such as ricin, abrin, modeccin, viscumin, pokeweed antiviral protein, saponin, momordin, and gelonin. These toxins contain a catalytic fragment and in some cases fragments or domains that recognize cell surface structures or facilitate translocation across cell membrane. Appropriately modified toxins are used which permit improved specificity without loss of potency. Conjugation of toxins to the antibodies is done by heterobifunctional crosslinkers, such as N-succinimidyl-3-(2-pyridyldithio)-propionate (SPDP) or 2-iminothiolane.

Prior to therapeutic use, conjugated antibodies are tested in view of their toxic potency, target specificity, in vitro and in-vivo stability and other properties (See e.g., Immunotoxins, Ed. Frankel, Kluwer Academic Publishers, Boston, 1988). It is desired that the toxicity of the conjugated agent, and the binding affinity and specificity of the antibody are minimally affected by the coupling procedures used. The conjugates are therefore tested for binding to the Tie-receptor (see Example 5). In-vitro toxicity toward target cells such as the leukemia cell line Dami is tested by measuring incorporation of labeled compounds in treated versus control conjugate-treated cell cultures, and more directly by determining cultures that are able to grow in clonogenic and cell growth back-extrapolation assays. In-vivo stability, clearance, and specific toxicity are judged by administration of conjugates to appropriate animal recipients, such as mice, rats, rabbits or monkeys. Further such recipients include normal mice and in-vivo tumor and leukemia xenograft models comprising human neoplastic cells introduced into immunodeficient strains of mice, such as the nude mouse or SCID mouse.

EXAMPLE 12

Preparation of Pharmaceutical Composition Containing Monoclonal Antibody 3C4C7G6

Pharmaceutical compositions of the present invention include an effective amount of the active ingredient, 3C4C7G6, alone or in combination with a suitable buffer, diluent and/or additive. Such compositions are provided as sterile aqueous solutions or as lyophilized or otherwise dried formulations. Typically, antibodies are formulated in such vehicles at concentrations from about 1 mg/ml to 10 mg/ml.

One example of a suitable pharmaceutical composition for injection contains monoclonal antibody 3C4C7G6 (1 mg/ml) in a buffered solution (pH 7.0 ±0.5) of monobasic sodium phosphate (0.45 mg/ml) and Tween 80 (0.2 mg/ml) in sterile H2O. Pharmaceutical compositions according to the invention are administered in doses determined by the skilled artisan upon consideration of the targeted disease, severity of symptoms, and characteristics of the patient. For example, pharmaceutical compositions of the invention may be applied locally to obtain maximum benefit in halting tumor growth and neovascularization or wound healing. However, different doses are necessary for cysteine use, depending upon characteristics of the patient, such as weight, age, progression of disease, metabolism, and others.

Additional embodiments will occur to the skilled artisan upon consideration of the foregoing detailed description. Accordingly, the present invention is limited only by the following claims.

We claim:

1. An antibody directed against a Tie-receptor tyrosine kinase extracellular domain.

2. A polyclonal antiserum comprising antibodies directed against a Tie-receptor tyrosine kinase extracellular domain.

3. A monoclonal antibody directed against a Tie-receptor tyrosine kinase extracellular domain.

4. A hybridoma cell line producing the monoclonal antibody according to claim 3.

5. The hybridoma cell line according to claim 4, wherein said hybridoma cell line is deposited as DSM accession number ACC2159.

6. A monoclonal antibody produced by the hybridoma cell line according to claim 5.

7. A detectably-labeled antibody according to claim 1, 3, or 6.

8. The detectably-labeled antibody according to claim 7, wherein said detectable label is selected from the group consisting of radioisotopes, dyes, enzymes, and biotin.

9. A method for detecting Tie-receptor tyrosine kinase (Tie) in a biological sample comprising the steps of:

a) contacting a biological sample suspected of containing Tie to a detectably-labeled anti-Tie antibody directed against a Tie-receptor tyrosine kinase extracellular domain, under conditions wherein said antibody forms an antibody-antigen complex with Tie;

b) washing the sample; and c) detecting the presence of said complex in said sample, wherein the detection of said complex is an indication of the presence of Tie in said biological sample.

10. A method for screening for neoplastic diseases characterized by proliferation of endothelial cells, comprising the steps of:

a) obtaining a tissue sample from a patient suspected of having a neoplastic disease characterized by proliferation of endothelial cells;

b) contacting said tissue sample to a detectably-labeled anti-Tie antibody directed against a Tie-receptor tyrosine kinase extracellular domain;

c) washing said tissue sample;

d) measuring the presence of said detectably-labeled anti-Tie antibody in said tissue sample to provide a measurement of anti-Tie antibodies in said tissue sample; and e) screening for neoplastic diseases characterized by proliferation of endothelial cells, wherein the presence of a neoplastic disease characterized by proliferation of endothelial cells is correlated to a measurement of anti-Tie antibodies in said tissue sample greater than a baseline measurement of anti-Tie antibodies, said baseline measurement derived from a tissue sample free of neoplastic diseases characterized by proliferation of endothelial cells.

11. The method of claim 9 wherein said biological sample comprises whole cells.

12. The method of claim 10 wherein said tissue sample comprises whole cells.

13. An antibody that specifically binds to a Tie-receptor tyrosine kinase.

14. An antibody according to claim 13 that binds to the carboxyl terminal tail of a Tie-receptor tyrosine kinase.

15. A polyclonal antiserum comprising antibodies according to claim 13.

16. A monoclonal antibody according to claim 13.

17. An antibody according to claim 16 further comprising a detectable label.

18. An antibody according to claim 17, wherein said detectable label is selected from the group consisting of radioisotopes, dyes, enzymes, and biotin.

19. A humanized monoclonal antibody according to claim 16.

20. A hybridoma capable of producing the monoclonal antibody of claim 16.

21. A method for detecting Tie-receptor tyrosine kinase (Tie) in a biological sample comprising the steps of:

a) contacting a biological sample suspected of containing Tie to an anti-Tie antibody according to any one of claims 1, 3, 13, 16, 19, under conditions wherein said antibody forms an antibody-antigen complex with Tie; and b) detecting the presence of said antibody-antigen complex in said biological sample, wherein the presence of said antibody-antigen complex in said biological sample is correlated with the presence of Tie in said biological sample.

22. A method according to claim 21 wherein said antibody is detectably-labeled.

23. A method according to claim 21 further comprising the step of washing said biological sample after said contacting step and before said detecting step, to remove uncomplexed antibody from said biological sample.

24. A method for detecting proliferation of vascular endothelial cells in a tissue sample, comprising the steps of:
   a) obtaining a tissue sample from a patient suspected of having a condition wherein vascular endothelial cells proliferate;
   b) contacting said tissue sample to an anti-Tie antibody according to any one of claims 1, 3, 13, 16, 19; and
   c) detecting said anti-Tie antibody in said tissue sample to provide a measurement of anti-Tie antibodies in said tissue sample, wherein the proliferation of endothelial cells is correlated to a measurement of anti-Tie antibodies in said tissue sample greater than a baseline measurement of anti-Tie antibodies, said baseline measurement derived from a tissue sample essentially free of proliferating endothelial cells.

25. A method according to claim 24 further comprising the step of washing said tissue sample after said contacting step and before said detecting step.

26. A method for screening for neoplastic diseases characterized by proliferation of endothelial cells, comprising the steps of:
   a) obtaining a tissue sample from a patient suspected of having a neoplastic disease characterized by proliferation of endothelial cells;
   b) contacting said tissue sample to an anti-Tie antibody according to any one of claims 1, 3, 13, 16, 19;
   c) measuring the presence of said anti-Tie antibody in said tissue sample to provide a measurement of anti-Tie antibodies in said tissue sample; and
   d) screening for neoplastic diseases characterized by proliferation of endothelial cells, wherein the presence of a disease characterized by proliferation of endothelial cells is correlated to a measurement of anti-Tie antibodies in said tissue sample greater than a baseline measurement of anti-Tie antibodies, said baseline measurement derived from a tissue sample free of neoplastic diseases characterized by proliferation of endothelial cells.

27. A method according to claim 26 further comprising the step of washing said tissue sample after said contacting step and before said detecting step.

28. An antiserum according to claim 2 or 15, wherein said antibodies are detectably labeled.

29. A method according to claim 11, further comprising the step of separating cells in said biological sample that express Tie receptor on their surface and form antigen-antibody complex with the anti-Tie antibody from cells in said biological sample which do not form antigen-antibody complex with the anti-Tie antibody.

30. A method according to claim 21 wherein the biological sample comprises a cell mixture suspected of including cells that express Tie receptor on their surface, and wherein the method further comprises the step of separating cells that express Tie receptor on their surface and form antigen-antibody complex with the anti-Tie antibody from cells which do not form antigen-antibody complex with the anti-Tie antibody.

31. An antiserum produced by a process comprising the steps of:
   immunizing a mammal with a composition comprising a polypeptide, said polypeptide comprising a Tie-receptor tyrosine kinase protein having the amino acid sequence set forth in SEQ ID NO: 5 or immunogenic fragment thereof; and
   obtaining antiserum from said mammal after said immunizing step, said antiserum containing antibodies that bind to a Tie-receptor tyrosine kinase protein.

32. An antiserum according to claim 31 wherein said polypeptide is purified prior to said immunizing step, and wherein said composition further includes an adjuvant.

33. Polyclonal antibodies purified from an antiserum according to any one of claims 2, 15, and 31, said polyclonal antibodies including antibodies that bind to a Tie-receptor tyrosine kinase.

* * * * *

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 24 base pairs
      (B) TYPE: nucleic acid
      (C) STRANDEDNESS: single
      (D) TOPOLOGY: linear

```
            (ii) MOLECULE TYPE: cDNA (xi) SEQUENCE DESCRIPTION: SEQ ID NO:1:

CGTAGATCTG GCGGTGGACC TGAC                                                  24

(2) INFORMATION FOR SEQ ID NO:2:

(i) SEQUENCE CHARACTERISTICS:
            (A) LENGTH: 56 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:2:

GGCCATGATC ACTAGTGATG GTGATGGTGA TGCTGCTGAT CCAGGCCCTC TTCAGC              56

(2) INFORMATION FOR SEQ ID NO:3:

(i) SEQUENCE CHARACTERISTICS:
            (A) LENGTH: 10 amino acids
            (B) TYPE: amino acid
            (C) STRANDEDNESS: Not Relevant
            (D) TOPOLOGY: linear (ii) MOLECULE TYPE: protein (xi) SEQUENCE DESCRIPTION: SEQ ID NO:3:

Ile Glu Gly Arg His His His His His His
        1               5                   10

(2) INFORMATION FOR SEQ ID NO:4:

(i) SEQUENCE CHARACTERISTICS:
            (A) LENGTH: 3845 base pairs
            (B) TYPE: nucleic acid
            (C) STRANDEDNESS: single
            (D) TOPOLOGY: linear (ii) MOLECULE TYPE: cDNA (ix) FEATURE:
            (A) NAME/KEY: CDS
            (B) LOCATION: 37..3450

(xi) SEQUENCE DESCRIPTION: SEQ ID NO:4:

CGCTCGTCCT GGCTGGCCTG GGTCGGCCTC TGGAGT ATG GTC TGG CGG GTG CCC          54
                                         Met Val Trp Arg Val Pro
                                          1               5

CCT TTC TTG CTC CCC ATC CTC TTC TTG GCT TCT CAT GTG GGC GCG GCG         102
Pro Phe Leu Leu Pro Ile Leu Phe Leu Ala Ser His Val Gly Ala Ala
            10                  15                  20

GTG GAC CTG ACG CTG CTG GCC AAC CTG CGG CTC ACG GAC CCC CAG CGC         150
Val Asp Leu Thr Leu Leu Ala Asn Leu Arg Leu Thr Asp Pro Gln Arg
        25                  30                  35

TTC TTC CTG ACT TGC GTG TCT GGG GAG GCC GGG GCG GGG AGG GGC TCG         198
Phe Phe Leu Thr Cys Val Ser Gly Glu Ala Gly Ala Gly Arg Gly Ser
    40                  45                  50

GAC GCC TGG GGC CCG CCC CTG CTG CTG GAG AAG GAC GAC CGT ATC GTG         246
Asp Ala Trp Gly Pro Pro Leu Leu Leu Glu Lys Asp Asp Arg Ile Val
55                  60                  65                  70

CGC ACC CCG CCC GGG CCA CCC CTG CGC CTG GCG CGC AAC GGT TCG CAC         294
Arg Thr Pro Pro Gly Pro Pro Leu Arg Leu Ala Arg Asn Gly Ser His
                75                  80                  85

CAG GTC ACG CTT CGC GGC TTC TCC AAG CCC TCG GAC CTC GTG GGC GTC         342
Gln Val Thr Leu Arg Gly Phe Ser Lys Pro Ser Asp Leu Val Gly Val
```

|                                                                      |      |
| -------------------------------------------------------------------- | ---- |
| TTC TCC TGC GTG GGC GGT GCT GGG GCG CGG CGC ACG CGC GTC ATC TAC       | 390  |
| Phe Ser Cys Val Gly Gly Ala Gly Ala Arg Arg Thr Arg Val Ile Tyr       |      |
|     105             110             115                              |      |
| GTG CAC AAC AGC CCT GGA GCC CAC CTG CTT CCA GAC AAG GTC ACA CAC       | 438  |
| Val His Asn Ser Pro Gly Ala His Leu Leu Pro Asp Lys Val Thr His       |      |
|     120             125             130                              |      |
| ACT GTG AAC AAA GGT GAC ACC GCT GTA CTT TCT GCA CGT GTG CAC AAG       | 486  |
| Thr Val Asn Lys Gly Asp Thr Ala Val Leu Ser Ala Arg Val His Lys       |      |
| 135             140             145             150                  |      |
| GAG AAG CAG ACA GAC GTG ATC TGG AAG AGC AAC GGA TCC TAC TTC TAC       | 534  |
| Glu Lys Gln Thr Asp Val Ile Trp Lys Ser Asn Gly Ser Tyr Phe Tyr       |      |
|         155             160             165                          |      |
| ACC CTG GAC TGG CAT GAA GCC CAG GAT GGG CGG TTC CTG CTG CAG CTC       | 582  |
| Thr Leu Asp Trp His Glu Ala Gln Asp Gly Arg Phe Leu Leu Gln Leu       |      |
|         170             175             180                          |      |
| CCA AAT GTG CAG CCA CCA TCG AGC GGC ATC TAC AGT GCC ACT TAC CTG       | 630  |
| Pro Asn Val Gln Pro Pro Ser Ser Gly Ile Tyr Ser Ala Thr Tyr Leu       |      |
|         185             190             195                          |      |
| GAA GCC AGC CCC CTG GGC AGC GCC TTC TTT CGG CTC ATC GTG CGG GGT       | 678  |
| Glu Ala Ser Pro Leu Gly Ser Ala Phe Phe Arg Leu Ile Val Arg Gly       |      |
|     200             205             210                              |      |
| TGT GGG GCT GGG CGC TGG GGG CCA GGC TGT ACC AAG GAG TGC CCA GGT       | 726  |
| Cys Gly Ala Gly Arg Trp Gly Pro Gly Cys Thr Lys Glu Cys Pro Gly       |      |
| 215             220             225             230                  |      |
| TGC CTA CAT GGA GGT GTC TGC CAC GAC CAT GAC GGC GAA TGT GTA TGC       | 774  |
| Cys Leu His Gly Gly Val Cys His Asp His Asp Gly Glu Cys Val Cys       |      |
|             235             240             245                      |      |
| CCC CCT GGC TTC ACT GGC ACC CGC TGT GAA CAG GCC TGC AGA GAG GGC       | 822  |
| Pro Pro Gly Phe Thr Gly Thr Arg Cys Glu Gln Ala Cys Arg Glu Gly       |      |
|             250             255             260                      |      |
| CGT TTT GGG CAG AGC TGC CAG GAG CAG TGC CCA GGC ATA TCA GGC TGC       | 870  |
| Arg Phe Gly Gln Ser Cys Gln Glu Gln Cys Pro Gly Ile Ser Gly Cys       |      |
|             265             270             275                      |      |
| CGG GGC CTC ACC TTC TGC CTC CCA GAC CCC TAT GGC TGC TCT TGT GGA       | 918  |
| Arg Gly Leu Thr Phe Cys Leu Pro Asp Pro Tyr Gly Cys Ser Cys Gly       |      |
|         280             285             290                          |      |
| TCT GGC TGG AGA GGA AGC CAG TGC CAA GAA GCT TGT GCC CCT GGT CAT       | 966  |
| Ser Gly Trp Arg Gly Ser Gln Cys Gln Glu Ala Cys Ala Pro Gly His       |      |
| 295             300             305             310                  |      |
| TTT GGG GCT GAT TGC CGA CTC CAG TGC CAG TGT CAG AAT GGT GGC ACT       | 1014 |
| Phe Gly Ala Asp Cys Arg Leu Gln Cys Gln Cys Gln Asn Gly Gly Thr       |      |
|             315             320             325                      |      |
| TGT GAC CGG TTC AGT GGT TGT GTC TGC CCC TCT GGG TGG CAT GGA GTG       | 1062 |
| Cys Asp Arg Phe Ser Gly Cys Val Cys Pro Ser Gly Trp His Gly Val       |      |
|         330             335             340                          |      |
| CAC TGT GAG AAG TCA GAC CGG ATC CCC CAG ATC CTC AAC ATG GCC TCA       | 1110 |
| His Cys Glu Lys Ser Asp Arg Ile Pro Gln Ile Leu Asn Met Ala Ser       |      |
|         345             350             355                          |      |
| GAA CTG GAG TTC AAC TTA GAG ACG ATG CCC CGG ATC AAC TGT GCA GCT       | 1158 |
| Glu Leu Glu Phe Asn Leu Glu Thr Met Pro Arg Ile Asn Cys Ala Ala       |      |
|         360             365             370                          |      |
| GCA GGG AAC CCC TTC CCC GTG CGG GGC AGC ATA GAG CTA CGC AAG CCA       | 1206 |
| Ala Gly Asn Pro Phe Pro Val Arg Gly Ser Ile Glu Leu Arg Lys Pro       |      |
| 375             380             385             390                  |      |
| GAC GGC ACT GTG CTC CTG TCC ACC AAG GCC ATT GTG GAG CCA GAG AAG       | 1254 |
| Asp Gly Thr Val Leu Leu Ser Thr Lys Ala Ile Val Glu Pro Glu Lys       |      |
|             395             400             405                      |      |
| ACC ACA GCT GAG TTC GAG GTG CCC CGC TTG GTT CTT GCG GAC AGT GGG       | 1302 |
| Thr Thr Ala Glu Phe Glu Val Pro Arg Leu Val Leu Ala Asp Ser Gly      |      |

-continued

|     |     |     | 410 |     |     |     | 415 |     |     |     | 420 |     |     |     |      |
| --- | --- | --- | --- | --- | --- | --- | --- | --- | --- | --- | --- | --- | --- | --- | ---- |
| TTC | TGG | GAG | TGC | CGT | GTG | TCC | ACA | TCT | GGC | GGC | CAA | GAC | AGC | CGG | CGC  | 1350 |
| Phe | Trp | Glu | Cys | Arg | Val | Ser | Thr | Ser | Gly | Gly | Gln | Asp | Ser | Arg | Arg  |
|     |     | 425 |     |     |     |     | 430 |     |     |     |     | 435 |     |     |      |

```
TTC AAG GTC AAT GTG AAA GTG CCC CCC GTG CCC CTG GCT GCA CCT CGG       1398
Phe Lys Val Asn Val Lys Val Pro Pro Val Pro Leu Ala Ala Pro Arg
        440             445             450

CTC CTG ACC AAG CAG AGC CGC CAG CTT GTG GTC TCC CCG CTG GTC TCG       1446
Leu Leu Thr Lys Gln Ser Arg Gln Leu Val Val Ser Pro Leu Val Ser
455             460             465                 470

TTC TCT GGG GAT GGA CCC ATC TCC ACT GTC CGC CTG CAC TAC CGG CCC       1494
Phe Ser Gly Asp Gly Pro Ile Ser Thr Val Arg Leu His Tyr Arg Pro
            475             480             485

CAG GAC AGT ACC ATG GAC TGG TCG ACC ATT GTG GTG GAC CCC AGT GAG       1542
Gln Asp Ser Thr Met Asp Trp Ser Thr Ile Val Val Asp Pro Ser Glu
        490             495             500

AAC GTG ACG TTA ATG AAC CTG AGG CCA AAG ACA GGA TAC AGT GTT CGT       1590
Asn Val Thr Leu Met Asn Leu Arg Pro Lys Thr Gly Tyr Ser Val Arg
        505             510             515

GTG CAG CTG AGC CGG CCA GGG GAA GGA GGA GAG GGG GCC TGG GGG CCT       1638
Val Gln Leu Ser Arg Pro Gly Glu Gly Gly Glu Gly Ala Trp Gly Pro
520             525             530

CCC ACC CTC ATG ACC ACA GAC TGT CCT GAG CCT TTG TTG CAG CCG TGG       1686
Pro Thr Leu Met Thr Thr Asp Cys Pro Glu Pro Leu Leu Gln Pro Trp
535             540             545                 550

TTG GAG GGC TGG CAT GTG GAA GGC ACT GAC CGG CTG CGA GTG AGC TGG       1734
Leu Glu Gly Trp His Val Glu Gly Thr Asp Arg Leu Arg Val Ser Trp
                555             560             565

TCC TTG CCC TTG GTG CCC GGG CCA CTG GTG GGC GAC GGT TTC CTG CTG       1782
Ser Leu Pro Leu Val Pro Gly Pro Leu Val Gly Asp Gly Phe Leu Leu
        570             575             580

CGC CTG TGG GAC GGG ACA CGG GGG CAG GAG CGG CGG GAG AAC GTC TCA       1830
Arg Leu Trp Asp Gly Thr Arg Gly Gln Glu Arg Arg Glu Asn Val Ser
        585             590             595

TCC CCC CAG GCC CGC ACT GCC CTC CTG ACG GGA CTC ACG CCT GGC ACC       1878
Ser Pro Gln Ala Arg Thr Ala Leu Leu Thr Gly Leu Thr Pro Gly Thr
        600             605             610

CAC TAC CAG CTG GAT GTG CAG CTC TAC CAC TGC ACC CTC CTG GGC CCG       1926
His Tyr Gln Leu Asp Val Gln Leu Tyr His Cys Thr Leu Leu Gly Pro
615             620             625             630

GCC TCG CCC CCT GCA CAC GTG CTT CTG CCC CCC AGT GGG CCT CCA GCC       1974
Ala Ser Pro Pro Ala His Val Leu Leu Pro Pro Ser Gly Pro Pro Ala
                635             640             645

CCC CGA CAC CTC CAC GCC CAG GCC CTC TCA GAC TCC GAG ATC CAG CTG       2022
Pro Arg His Leu His Ala Gln Ala Leu Ser Asp Ser Glu Ile Gln Leu
            650             655             660

ACA TGG AAG CAC CCG GAG GCT CTG CCT GGG CCA ATA TCC AAG TAC GTT       2070
Thr Trp Lys His Pro Glu Ala Leu Pro Gly Pro Ile Ser Lys Tyr Val
        665             670             675

GTG GAG GTG CAG GTG GCT GGG GGT GCA GGA GAC CCA CTG TGG ATA GAC       2118
Val Glu Val Gln Val Ala Gly Gly Ala Gly Asp Pro Leu Trp Ile Asp
680             685             690

GTG GAC AGG CCT GAG GAG ACA AGC ACC ATC ATC CGT GGC CTC AAC GCC       2166
Val Asp Arg Pro Glu Glu Thr Ser Thr Ile Ile Arg Gly Leu Asn Ala
695             700             705             710

AGC ACG CGC TAC CTC TTC CGC ATG CGG GCC AGC ATT CAG GGG CTC GGG       2214
Ser Thr Arg Tyr Leu Phe Arg Met Arg Ala Ser Ile Gln Gly Leu Gly
                715             720             725

GAC TGG AGC AAC ACA GTA GAA GAG TCC ACC CTG GGC AAC GGG CTG CAG       2262
Asp Trp Ser Asn Thr Val Glu Glu Ser Thr Leu Gly Asn Gly Leu Gln
```

-continued

|  |  |  | 730 |  |  |  | 735 |  |  |  | 740 |  |  |  |  |
|---|---|---|---|---|---|---|---|---|---|---|---|---|---|---|---|
| GCT | GAG | GGC | CCA | GTC | CAA | GAG | AGC | CGG | GCA | GCT | GAA | GAG | GGC | CTG | GAT | 2310
| Ala | Glu | Gly | Pro | Val | Gln | Glu | Ser | Arg | Ala | Ala | Glu | Glu | Gly | Leu | Asp |
|  |  | 745 |  |  |  |  | 750 |  |  |  |  | 755 |  |  |  |

CAG CAG CTG ATC CTG GCG GTG GTG GGC TCC GTG TCT GCC ACC TGC CTC  2358
Gln Gln Leu Ile Leu Ala Val Val Gly Ser Val Ser Ala Thr Cys Leu
        760             765             770

ACC ATC CTG GCC GCC CTT TTA ACC CTG GTG TGC ATC CGC AGA AGC TGC  2406
Thr Ile Leu Ala Ala Leu Leu Thr Leu Val Cys Ile Arg Arg Ser Cys
775             780             785             790

CTG CAT CGG AGA CGC ACC TTC ACC TAC CAG TCA GGC TCG GGC GAG GAG  2454
Leu His Arg Arg Arg Thr Phe Thr Tyr Gln Ser Gly Ser Gly Glu Glu
            795             800             805

ACC ATC CTG CAG TTC AGC TCA GGG ACC TTG ACA CTT ACC CGG CGG CCA  2502
Thr Ile Leu Gln Phe Ser Ser Gly Thr Leu Thr Leu Thr Arg Arg Pro
        810             815             820

AAA CTG CAG CCC GAG CCC CTG AGC TAC CCA GTG CTA GAG TGG GAG GAC  2550
Lys Leu Gln Pro Glu Pro Leu Ser Tyr Pro Val Leu Glu Trp Glu Asp
    825             830             835

ATC ACC TTT GAG GAC CTC ATC GGG GAG GGG AAC TTC GGC CAG GTC ATC  2598
Ile Thr Phe Glu Asp Leu Ile Gly Glu Gly Asn Phe Gly Gln Val Ile
840             845             850

CGG GCC ATG ATC AAG AAG GAC GGG CTG AAG ATG AAC GCA GCC ATC AAA  2646
Arg Ala Met Ile Lys Lys Asp Gly Leu Lys Met Asn Ala Ala Ile Lys
855             860             865             870

ATG CTG AAA GAG TAT GCC TCT GAA AAT GAC CAT CGT GAC TTT GCG GGA  2694
Met Leu Lys Glu Tyr Ala Ser Glu Asn Asp His Arg Asp Phe Ala Gly
            875             880             885

GAA CTG GAA GTT CTG TGC AAA TTG GGG CAT CAC CCC AAC ATC ATC AAC  2742
Glu Leu Glu Val Leu Cys Lys Leu Gly His His Pro Asn Ile Ile Asn
        890             895             900

CTC CTG GGG GCC TGT AAG AAC CGA GGT TAC TTG TAT ATC GCT ATT GAA  2790
Leu Leu Gly Ala Cys Lys Asn Arg Gly Tyr Leu Tyr Ile Ala Ile Glu
    905             910             915

TAT GCC CCC TAC GGG AAC CTG CTA GAT TTT CTG CGG AAA AGC CGG GTC  2838
Tyr Ala Pro Tyr Gly Asn Leu Leu Asp Phe Leu Arg Lys Ser Arg Val
920             925             930

CTA GAG ACT GAC CCA GCT TTT GCT CGA GAG CAT GGG ACA GCC TCT ACC  2886
Leu Glu Thr Asp Pro Ala Phe Ala Arg Glu His Gly Thr Ala Ser Thr
935             940             945             950

CTT AGC TCC CGG CAG CTG CTG CGT TTC GCC AGT GAT GCG GCC AAT GGC  2934
Leu Ser Ser Arg Gln Leu Leu Arg Phe Ala Ser Asp Ala Ala Asn Gly
            955             960             965

ATG CAG TAC CTG AGT GAG AAG CAG TTC ATC CAC AGG GAC CTG GCT GCC  2982
Met Gln Tyr Leu Ser Glu Lys Gln Phe Ile His Arg Asp Leu Ala Ala
        970             975             980

CGG AAT GTG CTG GTC GGA GAG AAC CTA GCC TCC AAG ATT GCA GAC TTC  3030
Arg Asn Val Leu Val Gly Glu Asn Leu Ala Ser Lys Ile Ala Asp Phe
    985             990             995

GGC CTT TCT CGG GGA GAG GAG GTT TAT GTG AAG AAG ACG ATG GGG CGT  3078
Gly Leu Ser Arg Gly Glu Glu Val Tyr Val Lys Lys Thr Met Gly Arg
    1000            1005            1010

CTC CCT GTG CGC TGG ATG GCC ATT GAG TCC CTG AAC TAC AGT GTC TAT  3126
Leu Pro Val Arg Trp Met Ala Ile Glu Ser Leu Asn Tyr Ser Val Tyr
1015            1020            1025            1030

ACC ACC AAG AGT GAT GTC TGG TCC TTT GGA GTC CTT CTT TGG GAG ATA  3174
Thr Thr Lys Ser Asp Val Trp Ser Phe Gly Val Leu Leu Trp Glu Ile
            1035            1040            1045

GTG AGC CTT GGA GGT ACA CCC TAC TGT GGC ATG ACC TGT GCC GAG CTC  3222
Val Ser Leu Gly Gly Thr Pro Tyr Cys Gly Met Thr Cys Ala Glu Leu

-continued

```
            1050                1055                1060
TAT GAA AAG CTG CCC CAG GGC TAC CGC ATG GAG CAG CCT CGA AAC TGT           3270
Tyr Glu Lys Leu Pro Gln Gly Tyr Arg Met Glu Gln Pro Arg Asn Cys
            1065                1070                1075

GAC GAT GAA GTG TAC GAG CTG ATG CGT CAG TGC TGG CGG GAC CGT CCC           3318
Asp Asp Glu Val Tyr Glu Leu Met Arg Gln Cys Trp Arg Asp Arg Pro
        1080                1085                1090

TAT GAG CGA CCC CCC TTT GCC CAG ATT GCG CTA CAG CTA GGC CGC ATG           3366
Tyr Glu Arg Pro Pro Phe Ala Gln Ile Ala Leu Gln Leu Gly Arg Met
1095                1100                1105                1110

CTG GAA GCC AGG AAG GCC TAT GTG AAC ATG TCG CTG TTT GAG AAC TTC           3414
Leu Glu Ala Arg Lys Ala Tyr Val Asn Met Ser Leu Phe Glu Asn Phe
                1115                1120                1125

ACT TAC GCG GGC ATT GAT GCC ACA GCT GAG GAG GCC TGAGCTGCCA                3460
Thr Tyr Ala Gly Ile Asp Ala Thr Ala Glu Glu Ala
            1130                1135

TCCAGCCAGA ACGTGGCTCT GCTGGCCGGA GCAAACTCTG CTGTCTAACC TGTGACCAGT         3520

CTGACCCTTA CAGCCTCTGA CTTAAGCTGC CTCAAGGAAT TTTTTTAACT TAAGGGAGAA         3580

AAAAAGGGAT CTGGGGATGG GGTGGGCTTA GGGGAACTGG GTTCCCATGC TTTGTAGGTG         3640

TCTCATAGCT ATCCTGGGCA TCCTTCTTTC TAGTTCAGCT GCCCCACAGG TGTGTTTCCC         3700

ATCCCACTGC TCCCCCAACA CAAACCCCCA CTCCAGCTCC TTCGCTTAAG CCAGCACTCA         3760

CACCACTAAC ATGCCCTGTT CAGCTACTCC CACTCCCGGC CTGTCATTCA GAAAAAAATA         3820

AATGTTCTAA TAAGCTCCAA AAAAA                                               3845
```

(2) INFORMATION FOR SEQ ID NO:5:

(i) SEQUENCE CHARACTERISTICS:
        (A) LENGTH: 1138 amino acids
        (B) TYPE: amino acid
        (D) TOPOLOGY: linear (ii) MOLECULE TYPE: protein (xi) SEQUENCE DESCRIPTION: SEQ ID NO:5:

```
Met Val Trp Arg Val Pro Pro Phe Leu Leu Pro Ile Leu Phe Leu Ala
 1               5                  10                  15

Ser His Val Gly Ala Ala Val Asp Leu Thr Leu Leu Ala Asn Leu Arg
                20                  25                  30

Leu Thr Asp Pro Gln Arg Phe Phe Leu Thr Cys Val Ser Gly Glu Ala
            35                  40                  45

Gly Ala Gly Arg Gly Ser Asp Ala Trp Gly Pro Leu Leu Leu Glu
        50                  55                  60

Lys Asp Asp Arg Ile Val Arg Thr Pro Pro Gly Pro Pro Leu Arg Leu
 65                  70                  75                  80

Ala Arg Asn Gly Ser His Gln Val Thr Leu Arg Gly Phe Ser Lys Pro
                85                  90                  95

Ser Asp Leu Val Gly Val Phe Ser Cys Val Gly Gly Ala Gly Ala Arg
            100                 105                 110

Arg Thr Arg Val Ile Tyr Val His Asn Ser Pro Gly Ala His Leu Leu
        115                 120                 125

Pro Asp Lys Val Thr His Thr Val Asn Lys Gly Asp Thr Ala Val Leu
    130                 135                 140

Ser Ala Arg Val His Lys Glu Lys Gln Thr Asp Val Ile Trp Lys Ser
145                 150                 155                 160

Asn Gly Ser Tyr Phe Tyr Thr Leu Asp Trp His Glu Ala Gln Asp Gly
                165                 170                 175
```

-continued

```
Arg Phe Leu Leu Gln Leu Pro Asn Val Gln Pro Ser Ser Gly Ile
            180                 185                 190

Tyr Ser Ala Thr Tyr Leu Glu Ala Ser Pro Leu Gly Ser Ala Phe Phe
        195                 200                 205

Arg Leu Ile Val Arg Gly Cys Gly Ala Gly Arg Trp Gly Pro Gly Cys
    210                 215                 220

Thr Lys Glu Cys Pro Gly Cys Leu His Gly Gly Val Cys His Asp His
225                 230                 235                 240

Asp Gly Glu Cys Val Cys Pro Pro Gly Phe Thr Gly Thr Arg Cys Glu
                245                 250                 255

Gln Ala Cys Arg Glu Gly Arg Phe Gly Gln Ser Cys Gln Glu Gln Cys
            260                 265                 270

Pro Gly Ile Ser Gly Cys Arg Gly Leu Thr Phe Cys Leu Pro Asp Pro
        275                 280                 285

Tyr Gly Cys Ser Cys Gly Ser Gly Trp Arg Gly Ser Gln Cys Gln Glu
    290                 295                 300

Ala Cys Ala Pro Gly His Phe Gly Ala Asp Cys Arg Leu Gln Cys Gln
305                 310                 315                 320

Cys Gln Asn Gly Gly Thr Cys Asp Arg Phe Ser Gly Cys Val Cys Pro
                325                 330                 335

Ser Gly Trp His Gly Val His Cys Glu Lys Ser Asp Arg Ile Pro Gln
            340                 345                 350

Ile Leu Asn Met Ala Ser Glu Leu Glu Phe Asn Leu Glu Thr Met Pro
        355                 360                 365

Arg Ile Asn Cys Ala Ala Ala Gly Asn Pro Phe Pro Val Arg Gly Ser
    370                 375                 380

Ile Glu Leu Arg Lys Pro Asp Gly Thr Val Leu Leu Ser Thr Lys Ala
385                 390                 395                 400

Ile Val Glu Pro Glu Lys Thr Thr Ala Glu Phe Glu Val Pro Arg Leu
                405                 410                 415

Val Leu Ala Asp Ser Gly Phe Trp Glu Cys Arg Val Ser Thr Ser Gly
            420                 425                 430

Gly Gln Asp Ser Arg Arg Phe Lys Val Asn Val Lys Val Pro Pro Val
        435                 440                 445

Pro Leu Ala Ala Pro Arg Leu Leu Thr Lys Gln Ser Arg Gln Leu Val
    450                 455                 460

Val Ser Pro Leu Val Ser Phe Ser Gly Asp Gly Pro Ile Ser Thr Val
465                 470                 475                 480

Arg Leu His Tyr Arg Pro Gln Asp Ser Thr Met Asp Trp Ser Thr Ile
                485                 490                 495

Val Val Asp Pro Ser Glu Asn Val Thr Leu Met Asn Leu Arg Pro Lys
            500                 505                 510

Thr Gly Tyr Ser Val Arg Val Gln Leu Ser Arg Pro Gly Glu Gly Gly
        515                 520                 525

Glu Gly Ala Trp Gly Pro Pro Thr Leu Met Thr Thr Asp Cys Pro Glu
    530                 535                 540

Pro Leu Leu Gln Pro Trp Leu Glu Gly Trp His Val Glu Gly Thr Asp
545                 550                 555                 560

Arg Leu Arg Val Ser Trp Ser Leu Pro Leu Val Pro Gly Pro Leu Val
                565                 570                 575

Gly Asp Gly Phe Leu Leu Arg Leu Trp Asp Gly Thr Arg Gly Gln Glu
            580                 585                 590

Arg Arg Glu Asn Val Ser Ser Pro Gln Ala Arg Thr Ala Leu Leu Thr
```

-continued

```
                595                 600                 605
Gly Leu Thr Pro Gly Thr His Tyr Gln Leu Asp Val Gln Leu Tyr His
    610                 615                 620
Cys Thr Leu Leu Gly Pro Ala Ser Pro Ala His Val Leu Leu Pro
625                 630                 635                 640
Pro Ser Gly Pro Pro Ala Pro Arg His Leu His Ala Gln Ala Leu Ser
                645                 650                 655
Asp Ser Glu Ile Gln Leu Thr Trp Lys His Pro Glu Ala Leu Pro Gly
                660                 665                 670
Pro Ile Ser Lys Tyr Val Val Glu Val Gln Val Ala Gly Gly Ala Gly
                675                 680                 685
Asp Pro Leu Trp Ile Asp Val Asp Arg Pro Glu Glu Thr Ser Thr Ile
    690                 695                 700
Ile Arg Gly Leu Asn Ala Ser Thr Arg Tyr Leu Phe Arg Met Arg Ala
705                 710                 715                 720
Ser Ile Gln Gly Leu Gly Asp Trp Ser Asn Thr Val Glu Glu Ser Thr
                725                 730                 735
Leu Gly Asn Gly Leu Gln Ala Glu Gly Pro Val Gln Glu Ser Arg Ala
                740                 745                 750
Ala Glu Glu Gly Leu Asp Gln Gln Leu Ile Leu Ala Val Val Gly Ser
                755                 760                 765
Val Ser Ala Thr Cys Leu Thr Ile Leu Ala Ala Leu Leu Thr Leu Val
770                 775                 780
Cys Ile Arg Arg Ser Cys Leu His Arg Arg Thr Phe Thr Tyr Gln
785                 790                 795                 800
Ser Gly Ser Gly Glu Glu Thr Ile Leu Gln Phe Ser Ser Gly Thr Leu
                805                 810                 815
Thr Leu Thr Arg Arg Pro Lys Leu Gln Pro Glu Pro Leu Ser Tyr Pro
                820                 825                 830
Val Leu Glu Trp Glu Asp Ile Thr Phe Glu Asp Leu Ile Gly Glu Gly
    835                 840                 845
Asn Phe Gly Gln Val Ile Arg Ala Met Ile Lys Lys Asp Gly Leu Lys
    850                 855                 860
Met Asn Ala Ala Ile Lys Met Leu Lys Glu Tyr Ala Ser Glu Asn Asp
865                 870                 875                 880
His Arg Asp Phe Ala Gly Glu Leu Glu Val Leu Cys Lys Leu Gly His
                885                 890                 895
His Pro Asn Ile Ile Asn Leu Leu Gly Ala Cys Lys Asn Arg Gly Tyr
                900                 905                 910
Leu Tyr Ile Ala Ile Glu Tyr Ala Pro Tyr Gly Asn Leu Leu Asp Phe
    915                 920                 925
Leu Arg Lys Ser Arg Val Leu Glu Thr Asp Pro Ala Phe Ala Arg Glu
    930                 935                 940
His Gly Thr Ala Ser Thr Leu Ser Ser Arg Gln Leu Leu Arg Phe Ala
945                 950                 955                 960
Ser Asp Ala Ala Asn Gly Met Gln Tyr Leu Ser Glu Lys Gln Phe Ile
                965                 970                 975
His Arg Asp Leu Ala Ala Arg Asn Val Leu Val Gly Glu Asn Leu Ala
                980                 985                 990
Ser Lys Ile Ala Asp Phe Gly Leu Ser Arg Gly Glu Glu Val Tyr Val
                995                 1000                1005
Lys Lys Thr Met Gly Arg Leu Pro Val Arg Trp Met Ala Ile Glu Ser
    1010                1015                1020
```

-continued

```
Leu Asn Tyr Ser Val Tyr Thr Thr Lys Ser Asp Val Trp Ser Phe Gly
1025             1030             1035             1040

Val Leu Leu Trp Glu Ile Val Ser Leu Gly Gly Thr Pro Tyr Cys Gly
            1045             1050             1055

Met Thr Cys Ala Glu Leu Tyr Glu Lys Leu Pro Gln Gly Tyr Arg Met
            1060             1065             1070

Glu Gln Pro Arg Asn Cys Asp Asp Glu Val Tyr Glu Leu Met Arg Gln
        1075             1080             1085

Cys Trp Arg Asp Arg Pro Tyr Glu Arg Pro Pro Phe Ala Gln Ile Ala
    1090             1095             1100

Leu Gln Leu Gly Arg Met Leu Glu Ala Arg Lys Ala Tyr Val Asn Met
1105             1110             1115             1120

Ser Leu Phe Glu Asn Phe Thr Tyr Ala Gly Ile Asp Ala Thr Ala Glu
                1125             1130             1135

Glu Ala
```